(12) United States Patent
Old et al.

(10) Patent No.: US 7,820,661 B2
(45) Date of Patent: *Oct. 26, 2010

(54) SUBSTITUTED GAMMA LACTAMS AS THERAPEUTICS AGENTS

(75) Inventors: David W. Old, Irvine, CA (US); Danny T. Dinh, Garden Grove, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/427,968

(22) Filed: Apr. 22, 2009

(65) Prior Publication Data

US 2009/0270392 A1 Oct. 29, 2009

Related U.S. Application Data

(60) Provisional application No. 61/047,501, filed on Apr. 24, 2008.

(51) Int. Cl.
| | |
|---|---|
| C07D 413/12 | (2006.01) |
| C07D 207/08 | (2006.01) |
| C07D 409/12 | (2006.01) |
| A61K 31/381 | (2006.01) |
| A61K 31/4025 | (2006.01) |
| A61K 31/402 | (2006.01) |
| A61K 31/5377 | (2006.01) |

(52) U.S. Cl. .................. 514/237.2; 514/422; 514/428; 514/429; 548/527; 548/574; 548/577; 544/141

(58) Field of Classification Search .................. None
See application file for complete search history.

(56) References Cited

U.S. PATENT DOCUMENTS

| | | | |
|---|---|---|---|
| 3,985,798 | A | 10/1976 | Floyd, Jr. et al. |
| 4,007,210 | A | 2/1977 | Bernady |
| 4,060,540 | A | 11/1977 | Bernady |
| 4,166,452 | A | 9/1979 | Generales |
| 4,256,108 | A | 3/1981 | Theeuwes |
| 4,265,874 | A | 5/1981 | Bonsen |
| 4,994,274 | A | 2/1991 | Chan |
| 5,028,624 | A | 7/1991 | Chan |
| 5,034,413 | A | 7/1991 | Chan |
| 5,446,041 | A | 8/1995 | Chan |
| 6,437,146 | B1 | 8/2002 | Hattori |
| 6,531,614 | B2 | 3/2003 | Conrow |
| 6,573,294 | B1 | 6/2003 | Old |
| 6,710,072 | B2 | 3/2004 | Burk |
| 7,091,231 | B2 | 8/2006 | Donde |
| 7,473,704 | B2 | 1/2009 | Old |
| 7,476,747 | B2 | 1/2009 | Old |
| 2003/0120079 | A1 | 6/2003 | Elworthy |
| 2006/0205800 | A1 | 9/2006 | Donde |
| 2007/0203222 | A1 | 8/2007 | Old |
| 2007/0219265 | A1 | 9/2007 | Old |
| 2007/0265330 | A1 | 11/2007 | Old |
| 2008/0039505 | A1 | 2/2008 | Old |
| 2008/0269498 | A1 | 10/2008 | Old |
| 2009/0286787 | A1* | 11/2009 | Old et al. .................. 514/235.5 |

FOREIGN PATENT DOCUMENTS

| | | |
|---|---|---|
| EP | 0308135 | 3/1989 |
| WO | WO 93/014743 | 8/1993 |
| WO | WO 95/19964 | 7/1995 |
| WO | WO 03/103604 | 12/2003 |
| WO | WO 2004/037813 | 5/2004 |
| WO | WO 2006/098918 | 9/2006 |
| WO | WO 2007/109578 | 9/2007 |
| WO | WO 2007/005176 | 11/2007 |
| WO | WO 2008/064039 | 5/2008 |

OTHER PUBLICATIONS

U.S. Appl. No. 12/524,803, filed Jul. 2009, Old et al.*
U.S. Appl. No. 12/323,077, filed Nov. 25, 2008, Old.
Bernady et al., 1977, CAS: 87:22543.
Bito, L.Z. Arch. Ophthalmol. Prostaglandins, Old Concepts and New Perspectives, vol. 105, pp. 1036-1039 (1987).
Bito, L.Z., Biological Protection with Prostaglandins, "Prostaglandins and Related Compounds as Potential Ocular Therapeutic Agents", vol. 1, Chapter 18, 1985, pp. 231-252.
Bito, L.Z., Glaucoma, Applied Pharmacology in the Medical Treatment, "Prostaglandins, Other Eicosanoids, and Their Derivatives as Potential Antiglaucoma Agents", 1984, Chapter 20, pp. 477-505.
Brawner et al. Prostaglandins and Congeners. 21. Synthesis of Some Cyclohexyl Analogs. XP002310257, Journal of Organic Chemistry, 44(1), 71-75, 1979.
Carey, Francis A.: Organic Chemistry, New York: McGraw-Hill Book Company 1987, p. 63.
Casy et al. Methyl 7-Hydroxyhept-5-Ynoate, Organic Synthesis, 415-420.
Crossley et al. Cyclohexane Analogs of the Prostaglandins. XP002310260, Tetrahedron Letters, (36), 3327-3330, 1971.
Kwon et al., Handbook of Essential Pharmacokinetics, Pharmacodynamics and Drug Metabolism from Industrial Scientists, 2001, http://www.my.ilibrary.com/Browse/open.asp?ID=4284 &loc=1, Retrieved from the Internet Jun. 16, 2008, p. 213.
Hareau et al, Synthesis of Optically Active 5-(Tert-Butyldimethylsiloxy)-2-Cyclohexenone and Its 6-Substituted Derivatives as Useful Chiral Building Blocks for the Synthesis of Cyclohexane Rings. Syntheses of Carone, Penienone, and Penihydrone, J. Am. Chem. Soc. 1999, 121, 3640-3650.
Lopez-Pelegrin et al, Solution- and Soluble-Polymer Supported Asymmetric Synthesis of Six-Membered Ring Prostanoids, Chem. Eur. J. 2000, 6, 1917-1922.
Metabolomics [Online], Retrieved from the Internet Jun. 16, 2008, www.en.wikipedia.org/wiki/Metabolomics.

(Continued)

*Primary Examiner*—Kamal A Saeed
*Assistant Examiner*—Michael Barker
(74) *Attorney, Agent, or Firm*—Kevin J. Forrestal; John E. Wurst; Doina G. Ene

(57) ABSTRACT

Therapeutic compounds, compositions, medicaments, and methods are disclosed herein.

21 Claims, No Drawings

OTHER PUBLICATIONS

Nilsson et al., Invest. Ophthalmol. Vis. Sci. (Suppl), 284 (1987), Arvo Abstracts 9-6:00.

Ohuchida et al. Synthesis of Thromboxane A2 Analogs-3. (+)-Thiathromboxane A2. XP002310259, Tetrahedron, 39(4), 4269-4272, 1983.

Remington's Pharmaceutical Sciences, Mack Publishing Company, Easton, PA., 16$^{th}$ Edition, 1980.

Siebold et al, Prodrug 5 3, Esterified Protaglandin Shows 'potent' Promise, 1989.

Stella, Valentino J. Expert Opinion of Therapeutic Patents, Prodrugs as Therapeutics, 2004 14(3):277-280.

Wolff et al., Burger's Medicinal Chemistry and Drug Discovery, 1994, Wiley-Interscience, Fifth Edition, vol. 1: Principles and Practice, pp. 975-977.

Resul, Bahram; et al.: Structure-Activity Relationships of Prostaglandin Analogues as Ocular Hypotensive Agents. Current Opinion in Therapeutic Patents, vol. 3, No. 6, Jan. 1, 1993, pp. 781-795.

* cited by examiner

SUBSTITUTED GAMMA LACTAMS AS THERAPEUTICS AGENTS

RELATED APPLICATION

This application claims the benefit of U.S. Provisional Application Ser. No. 61/047,501, filed Apr. 24, 2008, the disclosure of which is hereby incorporated in its entirety herein by reference

BACKGROUND OF THE INVENTION

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical β-adrenoreceptor antagonists have traditionally been the drugs of choice for treating glaucoma.

Certain eicosanoids and their derivatives are currently commercially available for use in glaucoma management. Eicosanoids and derivatives include numerous biologically important compounds such as prostaglandins and their derivatives. Prostaglandins can be described as derivatives of prostanoic acid which have the following structural formula:

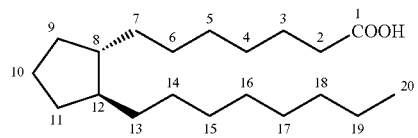

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by α or β [e.g. prostaglandin $F_{2\alpha}$ ($PGF_{2\beta}$)].

Prostaglandin $EP_2$ selective agonists are believed to have several medical uses. For example, U.S. Pat. No. 6,437,146 teaches the use of prostaglandin $EP_2$ selective agonists "for treating or preventing inflammation and pain in joint and muscle (e.g., rheumatoid arthritis, rheumatoid spondylitis, osteoarthritis, gouty arthritis, juvenile arthritis, etc.), inflammatory skin condition (e.g., sunburn, burns, eczema, dermatitis, etc.), inflammatory eye condition (e.g., conjunctivitis, etc.), lung disorder in which inflammation is involved (e.g., asthma, bronchitis, pigeon fancier's disease, farmer's lung, etc.), condition of the gastrointestinal tract associated with inflammation (e.g., aphthous ulcer, Chrohn's disease, atrophic gastritis, gastritis varialoforme, ulcerative colitis, coeliac disease, regional ileitis, irritable bowel syndrome, etc.), gingivitis, inflammation, pain and tumescence after operation or injury, pyrexia, pain and other conditions associated with inflammation, allergic disease, systemic lupus crythematosus, scleroderma, polymyositis, tendinitis, bursitis, periarteritis nodose, rheumatic fever, Sjgren's syndrome, Behcet disease, thyroiditis, type I diabetes, diabetic complication (diabetic microangiopathy, diabetic retinopathy, diabetic neohropathy, etc.), nephrotic syndrome, aplastic anemia, myasthenia gravis, uveitis contact dermatitis, psoriasis, Kawasaki disease, sarcoidosis, Hodgkin's disease, Alzheimers disease, kidney dysfunction (nephritis, nephritic syndrome, etc.), liver dysfunction (hepatitis, cirrhosis, etc.), gastrointestinal dysfunction (diarrhea, inflammatory bowel disease, etc.) shock, bone disease characterized by abnormal bone metabolism such as osteoporosis (especially, postmenopausal osteoporosis), hypercalcemia, hyperparathyroidism, Paget's bone diseases, osteolysis, hypercalcemia of malignancy with or without bone metastases, rheumatoid arthritis, periodonritis, osteoarthritis, ostealgia, osteopenia, cancer cachexia, calculosis, lithiasis (especially, urolithiasis), solid carcinoma, mesangial proliferative glomerulonephritis, edema (e.g. cardiac edema, cerebral edema, etc.), hypertension such as malignant hypertension or the like, premenstrual tension, urinary calculus, oliguria such as the one caused by acute or chronic failure, hyperphosphaturia, or the like."

U.S. Pat. No. 6,710,072 teaches the use of EP2 agonists for the treatment or prevention of "osteoporosis, constipation, renal disorders, sexual dysfunction, baldness, diabetes, cancer and in disorder of immune regulation . . . various pathophysiological diseases including acute myocardial infarction, vascular thrombosis, hypertension, pulmonary hypertension, ischemic heart disease, congestive heart failure, and angina pectoris."

SUMMARY OF THE INVENTION

Disclosed herein are compounds useful in treating glaucoma, inflammatory bowel disease, the stimulation of hair growth, and the stimulation of the conversion of vellus hair to terminal hair. The compounds themselves are disclosed below.

DESCRIPTION OF THE INVENTION

One embodiment is a compound according to the formula

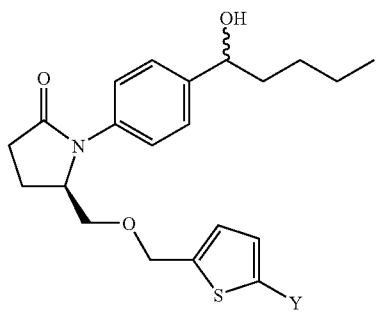

wherein Y is

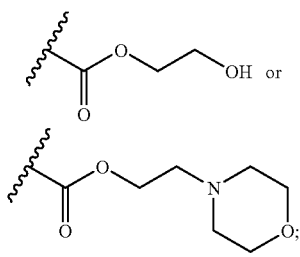

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

In another embodiment, said compound, and/or salt thereof, and/or prodrug thereof is used in the manufacture of a medicament for the treatment of baldness in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

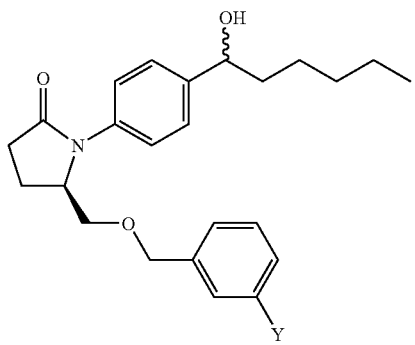

wherein Y is

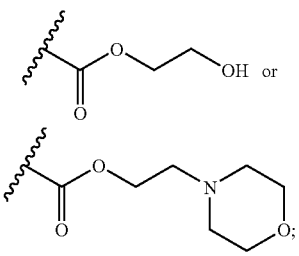

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

In another embodiment, said compound, and/or salt thereof, and/or prodrug thereof is used in the manufacture of a medicament for the treatment of baldness in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

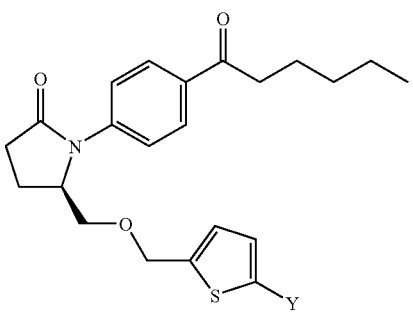

wherein Y is

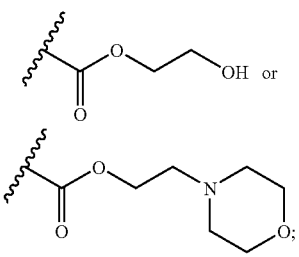

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

In another embodiment, said compound, and/or salt thereof, and/or prodrug thereof is used in the manufacture of a medicament for the treatment of baldness in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

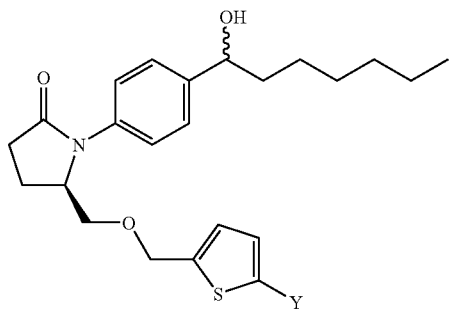

wherein Y is

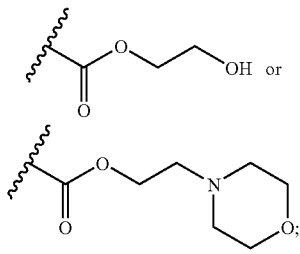

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

In another embodiment, said compound, and/or salt thereof, and/or prodrug thereof is used in the manufacture of a medicament for the treatment of baldness in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

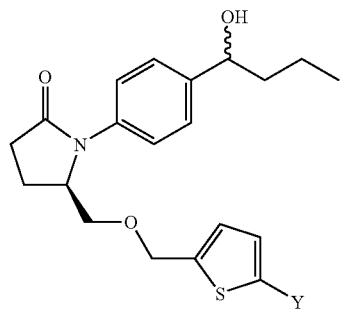

wherein Y is

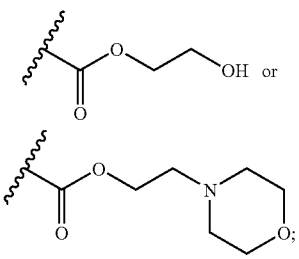

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

In another embodiment, said compound, and/or salt thereof, and/or prodrug thereof is used in the manufacture of a medicament for the treatment of baldness in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

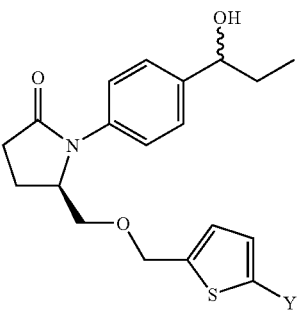

wherein Y is

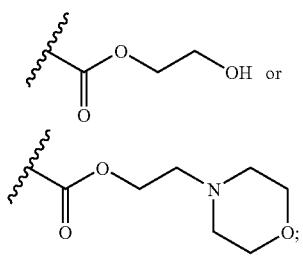

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

In another embodiment, said compound, and/or salt thereof, and/or prodrug thereof is used in the manufacture of a medicament for the treatment of baldness in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

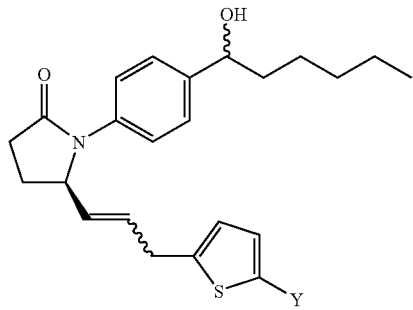

wherein Y is

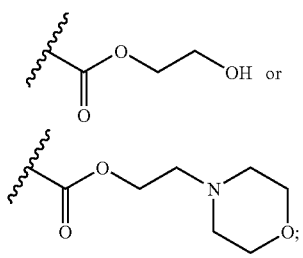

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

In another embodiment, said compound, and/or salt thereof, and/or prodrug thereof is used in the manufacture of a medicament for the treatment of baldness in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

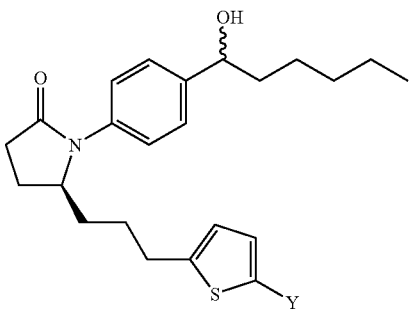

Y is

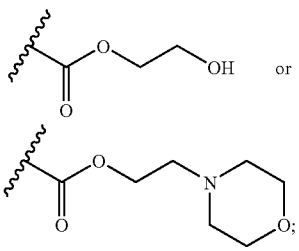

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

In another embodiment, said compound, and/or salt thereof, and/or prodrug thereof is used in the manufacture of a medicament for the treatment of baldness in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

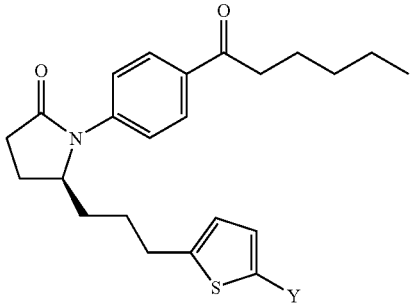

Y is

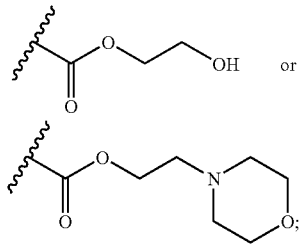

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

In another embodiment, said compound, and/or salt thereof, and/or prodrug thereof is used in the manufacture of a medicament for the treatment of baldness in a mammal.

Another embodiment is a composition comprising said compound, and/or salt thereof, and/or prodrug thereof, wherein said composition is ophthalmically acceptable. Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

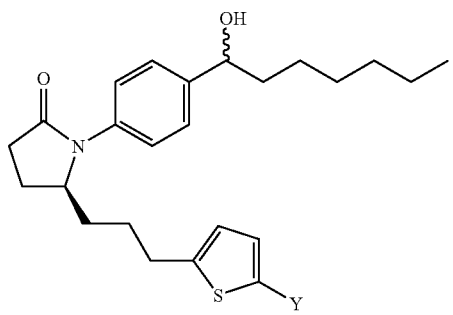

Y is

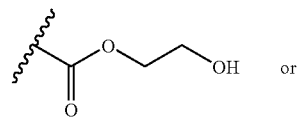

-continued

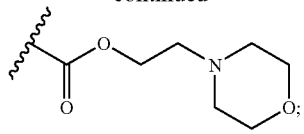

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

In another embodiment, said compound, and/or salt thereof, and/or prodrug thereof is used in the manufacture of a medicament for the treatment of baldness in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

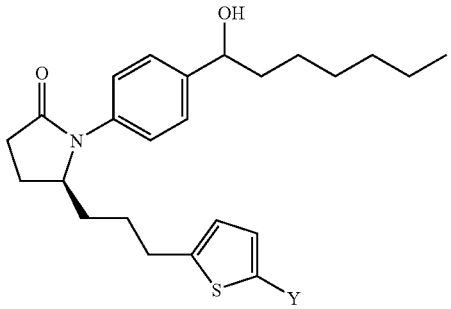

Y is

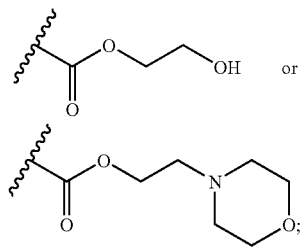

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

In another embodiment, said compound, and/or salt thereof, and/or prodrug thereof is used in the manufacture of a medicament for the treatment of baldness in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

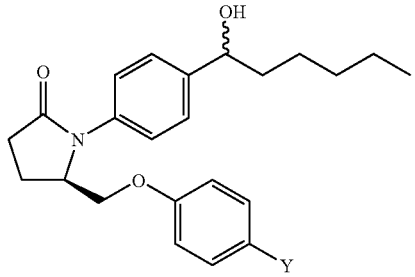

Y is

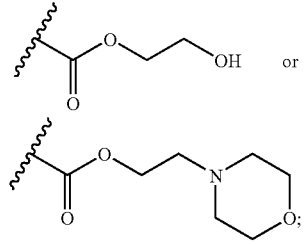

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

In another embodiment, said compound, and/or salt thereof, and/or prodrug thereof is used in the manufacture of a medicament for the treatment of baldness in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

The compounds disclosed herein are useful for the prevention or treatment of glaucoma or ocular hypertension in mammals, or for the manufacture of a medicament for the treatment of glaucoma or ocular hypertension. They are also useful for the treatment of those diseases disclosed in the art as being amenable to treatment by prostaglandin $EP_2$ agonist, such as the ones listed previously.

A "pharmaceutically acceptable salt" is any salt that retains the activity of the parent compound and does not impart any additional deleterious or untoward effects on the subject to which it is administered and in the context in which it is administered compared to the parent compound. A pharmaceutically acceptable salt also refers to any salt which may form in vivo as a result of administration of an acid, another salt, or a prodrug which is converted into an acid or salt.

Pharmaceutically acceptable salts of acidic functional groups may be derived from organic or inorganic bases. The salt may comprise a mono or polyvalent ion. Of particular interest are the inorganic ions, lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

A "prodrug" is a compound which is converted to a therapeutically active compound after administration, and the term should be interpreted as broadly herein as is generally understood in the art. While not intending to limit the scope of the invention, conversion may occur by hydrolysis of an ester group or some other biologically labile group. Generally, but not necessarily, a prodrug is inactive or less active than the therapeutically active compound to which it is converted. Ester prodrugs of the compounds disclosed herein are specifically contemplated. An ester may be derived from a carboxylic acid of C1 (i.e. the terminal carboxylic acid of a natural prostaglandin), or an ester may be derived from a carboxylic acid functional group on another part of the molecule, such as on a phenyl ring. While not intending to be limiting, an ester may be an alkyl ester, an aryl ester, or a heteroaryl ester. The term alkyl has the meaning generally understood by those skilled in the art and refers to linear, branched, or cyclic alkyl moieties. $C_{1-6}$ alkyl esters are particularly useful, where alkyl part of the ester has from 1 to 6 carbon atoms and includes, but is not limited to, methyl, ethyl, propyl, isopropyl, n-butyl, sec-butyl, iso-butyl, t-butyl, pentyl isomers, hexyl isomers, cyclopropyl, cyclobutyl, cyclopentyl, cyclohexyl, and combinations thereof having from 1-6 carbon atoms, etc.

A metabolite is broadly defined as a compound which is formed in vivo from the disclosed compound.

Those skilled in the art will readily understand that for administration or the manufacture of medicaments the compounds disclosed herein can be admixed with pharmaceutically acceptable excipients which per se are well known in the art. Specifically, a drug to be administered systemically, it may be confected as a powder, pill, tablet or the like, or as a solution, emulsion, suspension, aerosol, syrup or elixir suitable for oral or parenteral administration or inhalation.

For solid dosage forms or medicaments, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. The solid dosage forms may be uncoated or they may be coated by known techniques to delay disintegration and absorption in the gastrointestinal tract and thereby provide a sustained action over a longer period. For example, a time delay material such as glyceryl monostearate or glyceryl distcarate may be employed. They may also be coated by the technique described in the U.S. Pat. Nos. 4,256,108; 4,166,452; and 4,265,874 to form osmotic therapeutic tablets for control release. Liquid pharmaceutically administrable dosage forms can, for example, comprise a solution or suspension of one or more of the presently useful compounds and optional pharmaceutical adjutants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 16th Edition, 1980. The composition of the formulation to be administered, in any event, contains a quantity of one or more of the presently useful compounds in an amount effective to provide the desired therapeutic effect.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

The amount of the presently useful compound or compounds administered is, of course, dependent on the therapeutic effect or effects desired, on the specific mammal being treated, on the severity and nature of the mammal's condition, on the manner of administration, on the potency and pharmacodynamics of the particular compound or compounds employed, and on the judgment of the prescribing physician. The therapeutically effective dosage of the presently useful compound or compounds is preferably in the range of about 0.5 or about 1 to about 100 mg/kg/day.

A liquid which is ophthalmically acceptable is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions of the present invention include, but are not limited to, benzalkonium chloride, chlorobutanol, thimerosal, phenylmercuric acetate and phenylmercuric nitrate. A useful surfactant is, for example, Tween 80. Likewise, various useful vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. A useful chelating agent is edetate disodium, although other chelating agents may also be used in place or in conjunction with it.

The ingredients are usually used in the following amounts:

| Ingredient | Amount (% w/v) |
|---|---|
| active ingredient | about 0.001-5 |
| preservative | 0-0.10 |
| vehicle | 0-40 |
| tonicity adjustor | 1-10 |
| buffer | 0.01-10 |
| pH adjustor | q.s. pH 4.5-7.5 |
| antioxidant | as needed |
| surfactant | as needed |
| purified water | as needed to make 100% |

Applications for Stimulating Hair Growth

In one embodiment, the compounds disclosed herein can be useful in the treatment of baldness and/or hair loss. Alopecia (baldness) is a deficiency of either normal or abnormal hair, and is primarily a cosmetic problem in humans. It is a deficiency of terminal hair, the broad diameter, colored hair that is readily seen. However, in the so called bald person, although there is a noticeable absence of terminal hair, the skin does contain vellus hair, which is a fine colorless hair which may require microscopic examination to determine its presence. This vellus hair is a precursor to terminal hair.

The compounds described herein can be used to stimulate, such as the conversion of vellus hair to growth as terminal hair, as well as increasing the rate of growth of terminal hair. The utility of the compounds described herein for the simulation of hair growth was discovered as follows.

In the course of treating patients having glaucoma, treatment may only be appropriate in one eye. Within the course of daily practice, it was discovered that a patient who had been treated with bimatoprost, a prostaglandin analogue, developed lashed that were longer, thicker, and fuller in the treated eye than in the non-treated eye. On examination, the difference was found to be very striking. The lashes were longer and had a fuller, denser appearance in the treated eye. The lash appearance on the lids of the treated eyes would have appeared quite attractive if it represented a bilateral phenomenon. As a result of its asymmetric nature, the long lashes on one side could be construed as disturbing from a cosmetic standpoint. A systemic examination was preformed as a result of the asymmetric phenomenon. It soon became apparent that this altered appearance was not an isolated finding. Comparison of the lids of patients who were taking bimatoprost in only one eye revealed subtle changes in the lashed and adjacent hairs of the bimatoprost-treated side in several patients. Definite differences could be identified to varying degrees in the lashes and adjacent hairs of all patients who were taking the drug on a unilateral basis for longer than 6 months.

The changes in the lashes were apparent on gross inspection in several patients once attention was focused on the issue. In those with light colored hair and lashes, the differences were only seen easily with the aid of the high magnification and lighting capabilities of the slit lamp biomicroscope. In the course of glaucoma follow-up examination, attention is generally immediately focused on the eye itself. As a result of the high power magnification needed only one eye is seen at a time and the eye is seen at a high enough power that the lashes are not in focus. At these higher powers, any lash asymmetry between the two eyes is not likely to be noticed except by careful systematic comparison of the lashes and adjacent hairs of the eyelids of the two eyes.

Observed parameters leading to the conclusion that more robust hair growth occurred in the treatment area following administration of the prostaglandin analogue were multiple. They included increased length of lashed, increased number of lashes along the normal lash line, increased thickness and luster of lashes, increased auxiliary lash-like terminal hair in transitional areas adjacent to areas of normal lash growth, increased auxiliary lash-like terminal hairs at the medial and lateral canthal area, increased pigmentation of the lashes, increased numbers, increased length, as well as increased luster, and thickness of fine hair on the skin of the adjacent lid, and finally, increased perpendicular angulation of lashes and lash-like terminal hairs. The conclusion that hair growth is stimulated by prostaglandin analogues such as bimatoprost is thus supported not by evidence of a difference in a single parameter, but is based on multiple parameters of hair appearance in treated versus control areas in many subjects.

The compounds described herein are prostaglandin analogues and therefore have similar activities as bimatoprost, contain structural similarities, and therefore are expected to stimulate hair growth and stimulation of the conversion of vellus hair to terminal hair. In one embodiment, the compounds described herein and their prodrugs can be used for the stimulation of hair growth. As used herein, hair growth includes hair associated with the scalp, eyebrows, eyelids, beard, and other areas of the skin of animals.

In one embodiment, the compound is mixed with a dermatologically compatible vehicle or carrier. The vehicle, which may be employed for preparing compositions as described herein, may comprise, for example, aqueous solutions such as e.g., physiological salines, oil solutions, or ointments. The vehicle furthermore may contain dermatologically compatible preservatives such as e.g., benzalkonium chloride, surfactants like e.g., polysorbate 80, liposomes or polymers, for example, methyl cellulose, polyvinyl alcohol, polyvinyl pyrrolidone and hyaluronic acid; these may be used for increasing the viscosity. Furthermore, it is also possible to use soluble or insoluble drug inserts when the drug is to be administered.

In one embodiment, dermatological compositions can be formulated for topical treatment for the stimulation of hair growth which comprises an effective hair growth simulating amount of one or more compounds as defined above and a dermatologically compatible carrier. Effective amounts of the active compounds may be determined by one of ordinary skill in the art, but will vary depending on the compound employed, frequency of application and desired result. The compound will generally range from about 0.0000001 to about 50% by weight of the dermatological composition. Preferably, the compound will range from about 0.001 to about 50% by weight of total dermatological composition, more preferably from about 0.1 to about 30% by weight of the composition.

In one embodiment, the application of the present compounds for stimulation of hair growth finds applications in mammalian species, including both humans and animals. In humans, the compounds described herein can be applied for example, to the scalp, face beard, head, pubic area, upper lip, eyebrows, and eyelids. In animal raised for their pelts, e.g., mink, the compounds described herein can be applied over the entire surface of the body to improve the overall pelt for commercial reasons. The process can also be used for cosmetic reasons in animals, e.g., applied to the skin of dogs and cats having bald patches due to mange or other diseases causing a degree of alopecia.

The pharmaceutical compositions contemplated for the stimulation of hair growth include pharmaceutical compositions suited for topical and local action. The term "topical" as employed herein relates to the use of a compound, as described herein, incorporated in a suitable pharmaceutical carrier, and applied at the site of thinning hair or baldness for exertion of local action. Accordingly, such topical compositions include those pharmaceutical forms in which the compound is applied externally by direct contact with the skin to be treated. Conventional pharmaceutical forms for this purpose include ointments, liniments, creams, shampoos, lotions, pastes, jellies, sprays, aerosols, and the like, and may be applied in patches or impregnated dressings depending on the part of the body to be treated. The term "ointment" embraces formulations (including creams) having oleaginous, water-soluble and emulsion-type bases, e.g., petrolatum, lanolin, polyethylene glycols, as well as mixtures of these.

Typically, the compounds can be applied repeatedly for the sustained period of time topically on the part of the body to be treated, for example, the eyelids, eyebrows, skin or scalp. The preferred dosage regimen will generally involve regular, such as daily, administration for a period of treatment of at least one month, more preferably at least three months, and most preferably, at least six months.

For topical use on the eyelids or eyebrows, the active compounds can be formulated in aqueous solutions, creams, ointments, or oils exhibiting physologicla acceptable osmolarity by addition of pharmaceutically acceptable buffers and salts, such formulations may or may not, depending on the dispenser, contain preservatives such as benzalkonium chloride, chlorhexidine, chlorobutanol, parahydroxybenzoic acids and phenylmercuric salts such as nitrate, chloride, acetate, and borate, or antioxidants, as well as additives like EDTA, sorbitol, boric acid and the like as additives. Furthermore, particularly aqueous solutions may contain viscosity increasing agents such as polysaccharides, e.g., methylcellulose, mucopolysaccharides, e.g., hyaluronic acid and chondroitin sulfate, or poly alcohol, e.g., polyvinylalcohol. Various slow releasing gels and matricies may also be employed as well as soluble and insoluble ocular inserts, for instance, based on substances forming in situ gels. Depending on the actual formation and compound to be used, various amounts of the drug and different dose regimens may be employed. Typically, the daily amount of compound for treatment of the eyelid may be about 0.1 ng to about 100 mg per eyelid.

For topical use on the skin and scalp, the compound can be advantageously formulated using ointments, creams, liniments or patches as a carrier of the active ingredient. Also, these formulations may or may not contain preservatives, depending on the dispenser and nature of use. Such preservatives include those mentioned above, and methyl-, propyl-, or butyl-parahydroxybenzoic acid, betain, chlorhexidine, benzalkonium chloride, and the like. Various matricies for the slow release delivery may also be used. Typically, the dose to be applied on the scalp is in the range of about 0.1 ng to about 100 mg per day, more preferably about 1 ng to about 10 mg per day, and most preferably about 10 ng to about 1 mg per day depending on the compound and the formulation. To achieve the daily amount of medication depending on the formulation, the compound may be administered once or several times daily with or without antioxidants.

For topical use, creams, ointments, gels, solutions or suspensions, etc., containing the compound disclosed herein are employed. Topical formulations may generally be comprised of a pharmaceutical carrier, cosolvent, emulsifier, penetration enhancer, preservative system, and emollient.

The actual dose of the active compounds of the present invention depends on the specific compound, and on the condition to be treated; the selection of the appropriate dose is well within the knowledge of the skilled artisan.

The compounds disclosed herein are also useful in combination with other drugs useful for the treatment of glaucoma or other conditions.

EXAMPLES

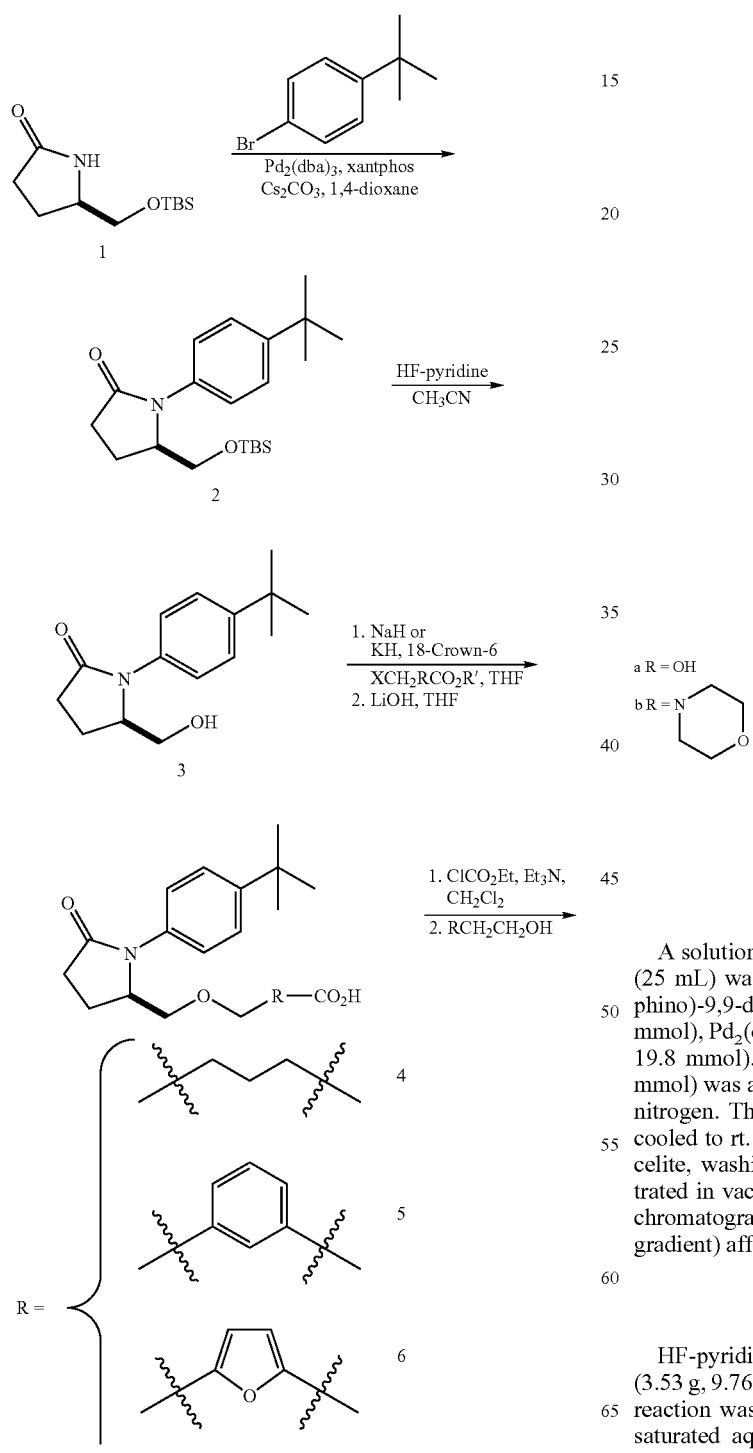

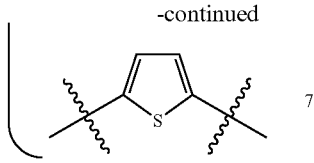

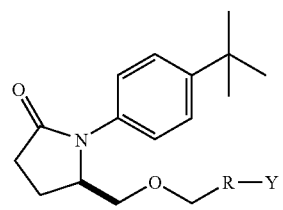

R =

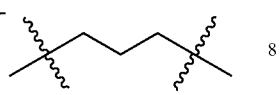 8

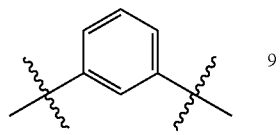 9

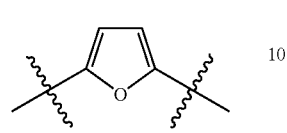 10

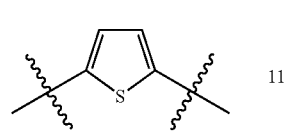 11 a R = OH
b R = N⌒O (morpholine)

Example 1

Step 1. Arylation of 1 to Give 2

A solution of amide 1 (3.30 g, 14.4 mmol) in 1,4-dioxane (25 mL) was added to a mixture of 4,5-bis(triphenylphosphino)-9,9-dimethylxanthene (xantphos, 600 mg, 1.04 mmol), $Pd_2(dba)_3$ (317 mg, 0.35 mmol) and $Cs_2CO_3$ (6.46 g, 19.8 mmol). 1-Bromo-4-tert-butylbenzene (2.40 mL, 13.8 mmol) was added and the reaction mixture was purged with nitrogen. The mixture was heated at reflux for 19 h, then cooled to rt. The reaction mixture was then filtered through celite, washing with $CH_2Cl_2$, and the filtrate was concentrated in vacuo. Purification of the residue by flash column chromatography on silica gel (10%→20% EtOAc/Hexane, gradient) afforded 3.53 g (71%) of the desired product 2.

Step 2. Deprotection of 2 to Give 3

HF-pyridine (5 mL) was added to a solution of silyl ether 2 (3.53 g, 9.76 mmol) in MeCN (20 mL) in a plastic bottle. The reaction was stirred at rt for 5 h, then was quenched with saturated aqueous $NaHCO_3$ (250 mL). The mixture was extracted with EtOAc (3×100 mL). The combined extracts were washed with brine (150 mL) then dried ($Na_2SO_4$), filtered and concentrated in vacuo to yield 2.14 g (89%) of the desired product 3.

Step 3. Alkylation of 3 to Give the Ester of 4

Sodium hydride (11 mg, 0.46 mmol) was added to a solution of alcohol 3 (100 mg, 0.40 mmol) in THF (3 mL) at 0° C. under nitrogen. After 1 h at 0° C., methyl 5-bromovalerate (67 μL, 0.47 mmol) was added and the reaction was allowed to warm to rt. After 3 h, tlc analysis showed mostly starting alcohol remaining and another portion of bromide (67 μL, 0.47 mmol) was added. After 22 h total reaction time, the reaction was quenched with 1 N HCl and extracted with EtOAc (3×25 mL). Combined extracts were dried ($Na_2SO_4$), filtered and concentrated in vacuo. Purification of the residue by flash column chromatography on silica gel (40% EtOAc/Hexane→EtOAc, gradient) afforded 19 mg (13%) of the desired ester.

Step 4. Saponification to Give 4

Aqueous lithium hydroxide (1 N, 0.5 mL) was added to a solution of ester from step 3 above (12.3 mg, 0.034 mmol) in THF (0.7 mL). After 2.5 h at rt, the reaction was acidified with 0.25 M HCl (5 mL) then extracted with $CH_2Cl_2$ (3×7 mL). Combined extracts were dried ($Na_2SO_4$), filtered and concentrated in vacuo to afford 10.2 mg (86%) of compound 4.

Step 5. Compounds 8a and 8b

Triethylamine and ethyl chloroformate are added sequentially to a solution of compound 4 in $CH_2Cl_2$ at room temperature. After 2.5 h, triethylamine and ethylene glycol are added. After stirring overnight at room temperature, the reaction mixture is partitioned between $H_2O$ and $CH_2Cl_2$. The phases are separated and the aqueous phase is extracted with $CH_2Cl_2$ (2×). The combined organic phase is washed with 1 N HCl then dried ($MgSO_4$), filtered and concentrated in vacuo. Purification of the residue by flash column chromatography on silica gel (10% $CH_3OH/CH_2Cl_2$) affords compound 8a.

Triethylamine and ethyl chloroformate are added sequentially to a solution of compound 4 in $CH_2Cl_2$ at room temperature. After 2.5 h, triethylamine and 4-(2-hydroxyethyl)-morphine are added. After stirring overnight at room temperature, the reaction mixture is partitioned between $H_2O$ and $CH_2Cl_2$. The phases are separated and the aqueous phase is extracted with $CH_2Cl_2$ (2×). The combined organic phase is washed with 1 N HCl then dried ($MgSO_4$), filtered and concentrated in vacuo. Purification of the residue by flash column chromatography on silica gel (10% $CH_3OH/CH_2Cl_2$) affords compound 8b.

Example 2

Step 1. Alkylation of 3 to Give the Ester of 5

Potassium hydride (23.4 mg, 0.58 mmol) and 18-crown-6 (167 mg, 0.63 mmol) were added sequentially to a solution of alcohol 3 (130 mg, 0.53 mmol) in THF (3 mL) at 0° C. After 1 h at 0° C., a solution of methyl 3-(chloromethyl)benzoate (prepared from the corresponding acid chloride, pyridine and methanol: see *J. Org. Chem.* 1988, 53, 2548-2552; 116 mg, 0.63 mmol) in THF (1.5 mL) was added via cannula and the reaction was allowed to warm to rt. After 22.5 h, the reaction was quenched with 0.1 N HCl (10 mL) and extracted with EtOAc (3×15 mL). Combined extracts were washed with saturated aqueous $NaHCO_3$ (15 mL) and brine (15 mL) then dried ($Na_2SO_4$), filtered and concentrated in vacuo. Purification of the residue by flash column chromatography on silica gel (30%→50% EtOAc/Hexane, gradient) afforded 66 mg (32%) of the desired ester.

Step 2. Saponification to Give 5

Aqueous lithium hydroxide (1 N, 0.4 mL) was added to a solution of ester from step 1 above (33.5 mg, 0.085 mmol) in THF (0.75 mL). After 3.5 h at rt, the reaction was acidified with 0.25 M HCl (5 mL) then extracted with $CH_2Cl_2$ (3×10 mL). Combined extracts were dried ($Na_2SO_4$), filtered and concentrated in vacuo. Purification of the residue by flash column chromatography on silica gel (2% $MeOH/CH_2Cl_2$), followed by preparative thin layer chromatography (10% $MeOH/CH_2Cl_2$) afforded 6.6 mg (20%) of compound 5.

Step 3. Compounds 9a and 9b

Compounds 9a and 9b are prepared from compound 5 according to Example 1, step 5.

Example 3

Step 1. Alkylation of 3 to Give the Ester of 6

Potassium hydride (27 mg, 0.67 mmol) and 18-crown-6 (193 mg, 0.73 mmol) were added sequentially to a solution of alcohol 3 (150 mg, 0.61 mmol) in THF (4 mL) at 0° C. After 1 h at 0° C., a solution of ethyl 5-chloromethylfuran-2-carboxylate (commercially available from Aldrich Chemical Company, 138 mg, 0.73 mmol) in THF (1 mL) was added via cannula and the reaction was allowed to warm to rt. After 18.5 h, the reaction was quenched with 0.25 N HCl (10 mL) and extracted with EtOAc (3×15 mL). Combined extracts were washed with brine (20 mL) then dried ($Na_2SO_4$), filtered and concentrated in vacuo. Purification of the residue by flash column chromatography on silica gel (20%→50% EtOAc/Hexane, gradient) afforded 78 mg (32%) of the desired ester.

Step 2. Saponification to Give 6

Aqueous lithium hydroxide (1 N, 0.5 mL) was added to a solution of ester from step 1 above (66.7 mg, 0.17 mmol) in THF (0.5 mL). After 3 h at rt, the reaction was acidified with 1 N HCl (2 mL) then extracted with $CH_2Cl_2$ (3×10 mL). Combined extracts were dried ($Na_2SO_4$), filtered and concentrated in vacuo to afford 54.4 mg (88%) of compound 6.

Step 3. Compounds 10a and 10b

Compounds 10a and 10b are prepared from compound 6 according to Example 1, step 5.

Example 4

Step 1. Alkylation of 3 to Give the Ester of 7

Potassium hydride (25.2 mg, 0.63 mmol) and 18-crown-6 (181 mg, 0.68 mmol) were added sequentially to a solution of alcohol 3 (140 mg, 0.57 mmol) in THF (4 mL) at 0° C. After 1.5 h at 0° C., a solution of methyl 5-chloromethylthiophene-2-carboxylate (prepared according to the procedures described in WO2004/037808; 130 mg, 0.68 mmol) in THF (1.5 mL) was added via cannula and the reaction was allowed to warm to rt. After 20 h, the reaction was quenched with 0.25

N HCl (15 mL) and extracted with EtOAc (3×20 mL). Combined extracts were washed with brine (30 mL) then dried (Na$_2$SO$_4$), filtered and concentrated in vacuo. Purification of the residue by flash column chromatography on silica gel (20%→50% EtOAc/Hexane, gradient) afforded 40.7 mg (18%) of the desired ester.

Step 2. Saponification to Give 7

Aqueous lithium hydroxide (1 N, 0.4 mL) was added to a solution of ester from step 1 above (37 mg, 0.092 mmol) in THF (0.75 mL). After 18 h at rt, the reaction was acidified with 1 N HCl (7 mL) then extracted with CH$_2$Cl$_2$ (3×10 mL). Combined extracts were dried (Na$_2$SO$_4$), filtered and concentrated in vacuo to afford 22.3 mg (62%) of compound 7.

Step 3. Compounds 11a and 11b

Compounds 11a and 11b are prepared from compound 7 according to Example 1, step 5.

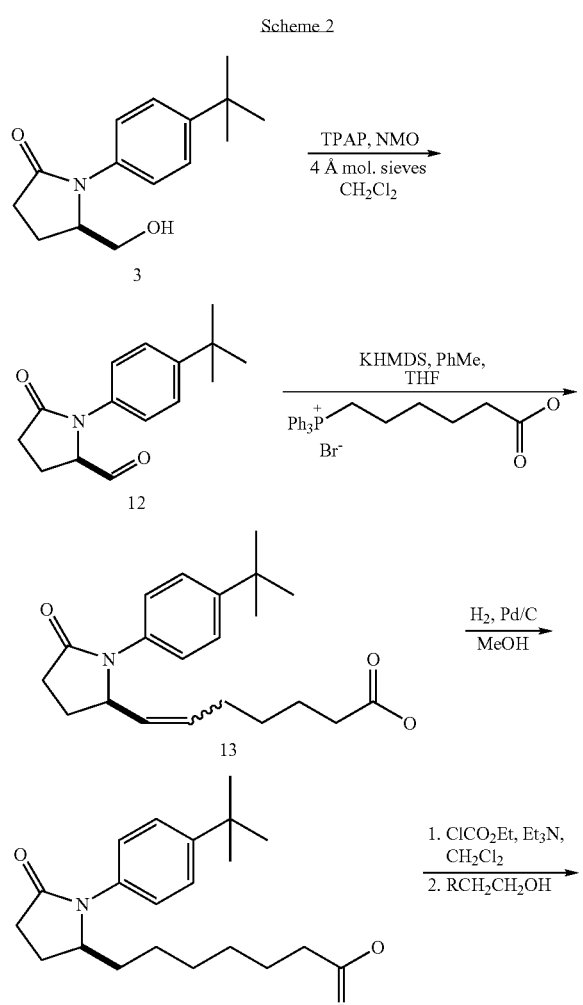

Scheme 2

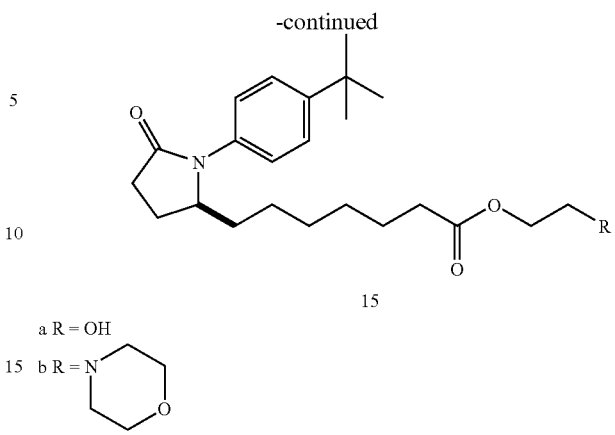

a R = OH
b R = N(morpholine)

Example 5

Step 1. Oxidation of 3 to Give Aldehyde 12

Molecular sieves (4 Å, 300 mg), 4-methylmorpholine N-oxide (427 mg, 3.64 mmol) and tetrapropylammonium perruthenate (250 mg, 0.71 mmol) were added sequentially to a solution of alcohol 3 (600 mg, 2.43 mmol) in CH$_2$Cl$_2$ (15 mL) at rt. After 23 h, the reaction mixture was filtered through celite, washing with CH$_2$Cl$_2$ (10 mL). The filtrate was concentrated in vacuo. Purification of the residue by flash column chromatography on silica gel (CH$_2$Cl$_2$→10% EtOAc/CH$_2$Cl$_2$, gradient) afforded 92 mg (15%) of the desired aldehyde 12.

Step 2. Wittig Reaction of 12 to Give 13

Potassium bis(trimethylsilyl)amide (0.5 M in PhMe, 1.92 mL, 0.96 mmol) was added to a solution of aldehyde 12 (86 mg, 0.35 mmol) in THF (2 mL) at rt. After 15 min at rt, the reaction mixture was cooled to −55° C. for 10 min before a solution of 5-carboxypentyltriphenylphosphonium bromide (207 mg, 0.45 mmol) was added via cannula. After 10 min at −55° C., the reaction was allowed to warm to rt. After 18 h at rt, the reaction was quenched with saturated aqueous NH$_4$Cl (15 mL) and extracted with EtOAc (3×15 mL). Combined extracts were washed with brine (20 mL), dried (Na$_2$SO$_4$), filtered and concentrated in vacuo. Purification of the residue by preparative thin layer chromatography (5% MeOH/CH$_2$Cl$_2$) afforded 10.5 mg (9%) of desired alkene 13.

Step 3. Hydrogenation of 13 to Give 14

Palladium on carbon (10 wt. %, 2 mg) was added to a solution of alkene 13 (5.8 mg, 0.017 mmol) in MeOH (1 mL). A hydrogen atmosphere was established by evacuating and refilling with hydrogen (3×) and the reaction mixture was stirred under a balloon of hydrogen for 18 h. The reaction mixture was filtered through celite, washing with MeOH, and the filtrate was concentrated in vacuo to afford 4.1 mg (70%) of compound 14.

Step 4. Compounds 15a and 15b

Compounds 15a and 15b are prepared from compound 14 according to Example 1, step 5.

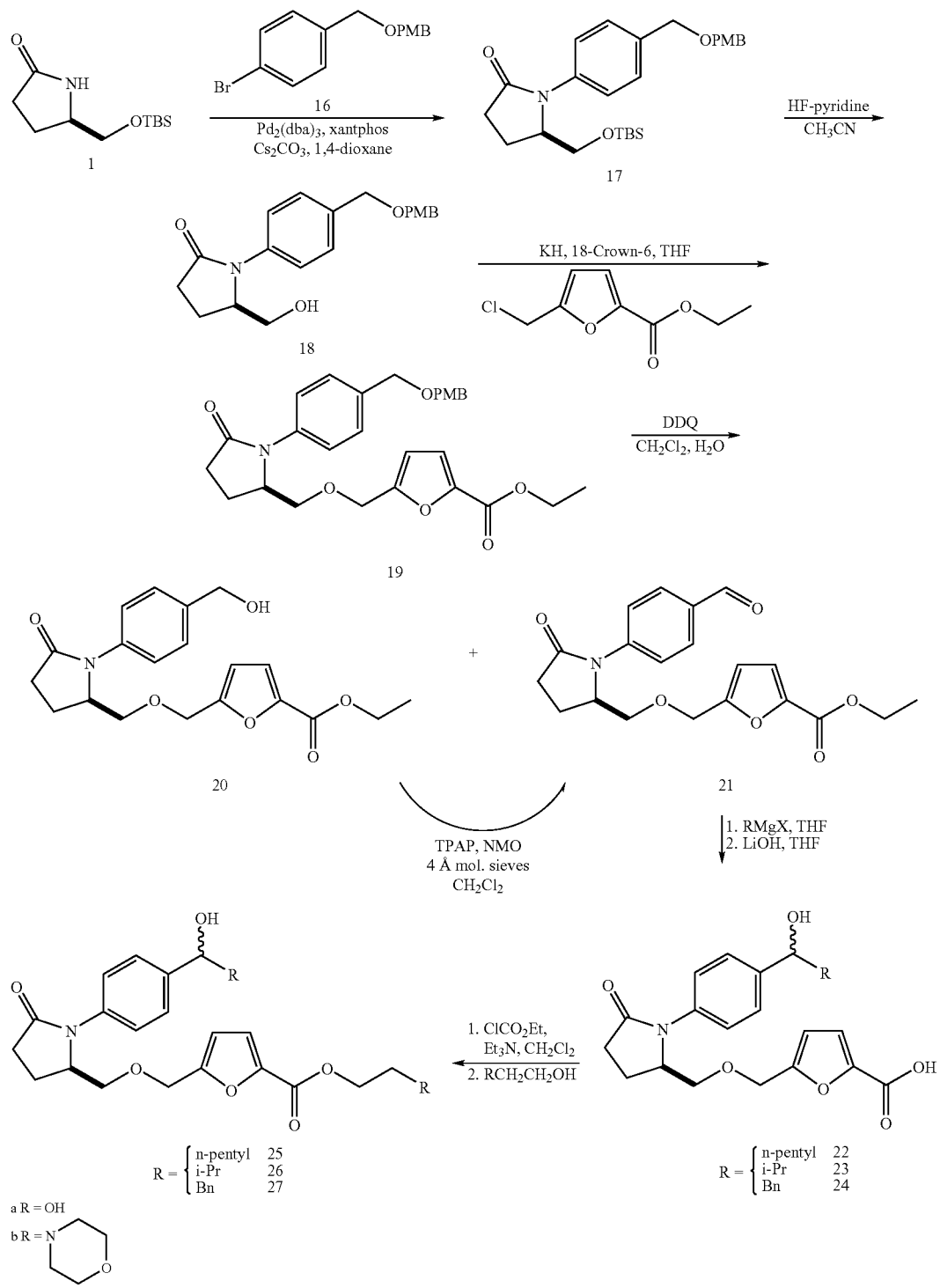

Example 6

Step 1. Arylation of 1 to Give 17

A solution of amide 1 (2.89 g, 12.60 mmol) in 1,4-dioxane (20 mL) followed by a solution of 1-(4-methoxybenzyloxym-ethyl)-4-bromobenzene (16: for synthesis, see U.S. Pat. No. 7,091,231, incorporated herein by reference; 3.88 g, 12.63 mmol) were added sequentially to a mixture of xantphos (877 mg, 1.52 mmol), $Pd_2(dba)_3$ (463 mg, 0.51 mmol) and $Cs_2CO_3$ (3.2 g, 9.82 mmol) via cannula. The reaction mixture was purged with nitrogen and then heated at reflux for 22 h. The reaction mixture was allowed to cool to rt then filtered through celite, washing with $CH_2Cl_2$, and the filtrate was concentrated in vacuo. Purification of the residue by flash column chromatography on silica gel (5%→25% EtOAc/Hexane, gradient) afforded 1.70 g (30%) of desired product 17.

Step 2. Deprotection of 17 to Give 18

HF-pyridine (5 mL) was added to a solution of silyl ether 17 (1.38 g, 3.03 mmol) in MeCN (15 mL) in a plastic bottle at 0° C. The reaction was stirred at 0° C. for 3 h, then was quenched with saturated aqueous $NaHCO_3$ (250 mL). The mixture was extracted with EtOAc (3×100 mL). The combined extracts were washed with brine (100 mL) then dried ($Na_2SO_4$), filtered and concentrated in vacuo. Purification of the residue by flash column chromatography on silica gel (1%→3% $MeOH/CH_2Cl_2$, gradient) afforded 464 mg (45%) of desired alcohol 18.

Step 3. Alkylation of Alcohol 18 to Give 19

Potassium hydride (44 mg, 1.10 mmol) and 18-crown-6 (365 mg, 1.38 mmol) were added sequentially to a solution of alcohol 18 (315 mg, 0.92 mmol) in THF (4 mL) at 0° C. After 1 h at 0° C., ethyl 5-chloromethylfuran-2-carboxylate (0.28 mL, 1.82 mmol) was added and the reaction was allowed to warm to rt. After 22 h, the reaction was quenched with 0.5 N HCl (20 mL) and extracted with EtOAc (3×25 mL). Combined extracts were washed with brine (50 mL) then dried ($Na_2SO_4$), filtered and concentrated in vacuo. Purification of the residue by flash column chromatography on silica gel (20% EtOAc/Hexane→EtOAc, gradient) afforded 148 mg (32%) of desired product 19.

Step 4. Oxidative Deprotection of 19 to Give 20 and 21

2,3-Dichloro-5,6-dicyano-1,4-benzoquinone (DDQ, 82 mg, 0.36 mmol) was added to a mixture of 19 (143 mg, 0.29 mmol) in $CH_2Cl_2$ (4 mL) and water (0.2 mL). After 3 h, tlc indicated that starting material remained and another portion of DDQ (82 mg, 0.36 mmol) was added. After a further 1.25 h, the reaction was quenched with saturated aqueous $NaHCO_3$ (20 mL). The mixture was extracted with EtOAc (3×20 mL). The combined extracts were washed with brine (20 mL) then dried ($Na_2SO_4$), filtered and concentrated in vacuo. Purification of the residue by flash column chromatography on silica gel ($CH_2Cl_2$→3% $MeOH/CH_2Cl_2$, gradient) afforded 38 mg (35%) of the desired alcohol 20 and 61 mg of impure aldehyde 21. Aldehyde 21 was further purified by preparative thin layer chromatography (5% $MeOH/CH_2Cl_2$) to afford 48.7 mg (45%) of aldehyde 21.

Step 5. Oxidation of 20 to Give 21

Molecular sieves (4 Å, 3 mg), 4-methylmorpholine N-oxide (12.6 mg, 0.11 mmol) and tetrapropylammonium perruthenate (2.5 mg, 0.007 mmol) were added sequentially to a solution of alcohol 20 (26.8 mg, 0.072 mmol) in $CH_2Cl_2$ (1.5 mL) at rt. After 20 min, the reaction mixture was filtered through celite, washing with $CH_2Cl_2$ (5 mL). The filtrate was concentrated in vacuo. Purification of the residue by preparative thin layer chromatography (5% $MeOH/CH_2Cl_2$) afforded 9.6 mg (36%) of the desired aldehyde 21.

Step 6. Grignard Reaction with 21 to Give the Ester of 22

Pentyl magnesium bromide (2.0 M in $Et_2O$, 32 L, 0.064 mmol) was added to a solution of aldehyde 21 (21.7 mg, 0.058 mmol) in THF (0.4 mL) at −40° C. under nitrogen. After 25 min, the reaction was quenched with saturated aqueous $NH_4Cl$ and extracted with $CH_2Cl_2$ (3×7 mL). Combined extracts were dried ($Na_2SO_4$), filtered and concentrated in vacuo. Purification of the residue by preparative thin layer chromatography (5% $MeOH/CH_2Cl_2$) afforded 10.6 mg (41%) of the desired ester.

Step 7. Saponification to Give 22

Aqueous lithium hydroxide (1 N, 0.1 mL) was added to a solution of ester from step 6 above (8.8 mg, 0.02 mmol) in THF (0.2 mL). After 1 h at rt, the reaction was acidified with 0.5 N HCl (1 mL) then extracted with $CH_2Cl_2$ (3×7 mL). Combined extracts were dried ($Na_2SO_4$), filtered and concentrated in vacuo to afford 8.2 mg (99%) of compound 22.

Step 8. Compounds 25a and 25b

Compounds 25a and 25b are prepared from compound 22 according to Example 1, step 5.

Example 7

Step 1. Grignard Reaction with 21 to Give the Ester of 23

Isopropyl magnesium chloride (2.0 M in THF, 31 L, 0.062 mmol) was added to a solution of aldehyde 21 (20.5 mg, 0.055 mmol) in THF (0.4 mL) at −40° C. under nitrogen. After 35 min, the reaction was quenched with saturated aqueous $NH_4Cl$ and extracted with $CH_2Cl_2$ (3×7 mL). Combined extracts were dried ($Na_2SO_4$), filtered and concentrated in vacuo. Purification of the residue by preparative thin layer chromatography (5% $MeOH/CH_2Cl_2$) afforded 5 mg (22%) of the desired ester.

Step 2. Saponification to Give 23

Aqueous lithium hydroxide (1 N, 0.05 mL) was added to a solution of the ester from step 1 above (3.1 mg, 0.007 mmol) in THF (0.15 mL). After 1 h at rt, the reaction was acidified with 0.2 N HCl (1 mL) then extracted with $CH_2Cl_2$ (3×7 mL). Combined extracts were dried ($Na_2SO_4$), filtered and concentrated in vacuo to afford 2.5 mg (86%) of compound 23.

Step 3. Compounds 26a and 26b

Compounds 26a and 26b are prepared from compound 23 according to Example 1, step 5.

Example 8

Step 1. Grignard Reaction with 21 to Give the Ester of 24

Benzyl magnesium chloride (2.0 M in THF, 14 μL, 0.028 mmol) was added to a solution of aldehyde 21 (9.6 mg, 0.026 mmol) in THF (0.3 mL) at −40° C. under nitrogen. After 45 min, the reaction was warmed to 0° C. After 25 min at 0° C., the reaction was quenched with saturated aqueous NH₄Cl and extracted with CH₂Cl₂ (3×7 mL). Combined extracts were dried (Na₂SO₄), filtered and concentrated in vacuo. Purification of the residue by preparative thin layer chromatography (7% MeOH/CH₂Cl₂) afforded 3.3 mg (28%) of the desired ester.

Step 2. Saponification to Give 24

Aqueous lithium hydroxide (1 N, 0.05 mL) was added to a solution of the ester from step 1 above (2.4 mg, 0.005 mmol) in THF (0.15 mL). After 2.5 h at rt, the reaction was acidified with 0.2 N HCl (1 mL) then extracted with CH₂Cl₂ (3×7 mL). Combined extracts were dried (Na₂SO₄), filtered and concentrated in vacuo to afford 2.2 mg (98%) of compound 24.

Step 3. Compounds 27a and 27b

Compounds 27a and 27b are prepared from compound 24 according to Example 1, step 5.

Example 9

Step 1. Alkylation of 18 to Give 28

Potassium hydride (55.5 mg, 1.38 mmol) and 18-crown-6 (456 mg, 1.73 mmol) were added sequentially to a solution of alcohol 18 (394 mg, 1.15 mmol) in THF (5 mL) at 0° C. After 1 h at 0° C., a solution of methyl 5-chloromethylthiophene-2-carboxylate (439 mg, 2.30 mmol) in THF (2 mL) was added via cannula and the reaction was allowed to warm to rt. After 19 h, tlc analysis showed starting material remained. Another portion of KH (20 mg, 0.50 mmol) was added and the reaction was heated at 50° C. After 2 h at 50° C., the reaction was cooled and quenched with 0.5 N HCl (20 mL) and extracted with EtOAc (3×25 mL). Combined extracts were washed with brine (50 mL) then dried (Na₂SO₄), filtered and concentrated in vacuo. Purification of the residue by flash column chromatography on silica gel (15% EtOAc/Hexane→EtOAc, gradient) afforded 108 mg (19%) of desired product 28.

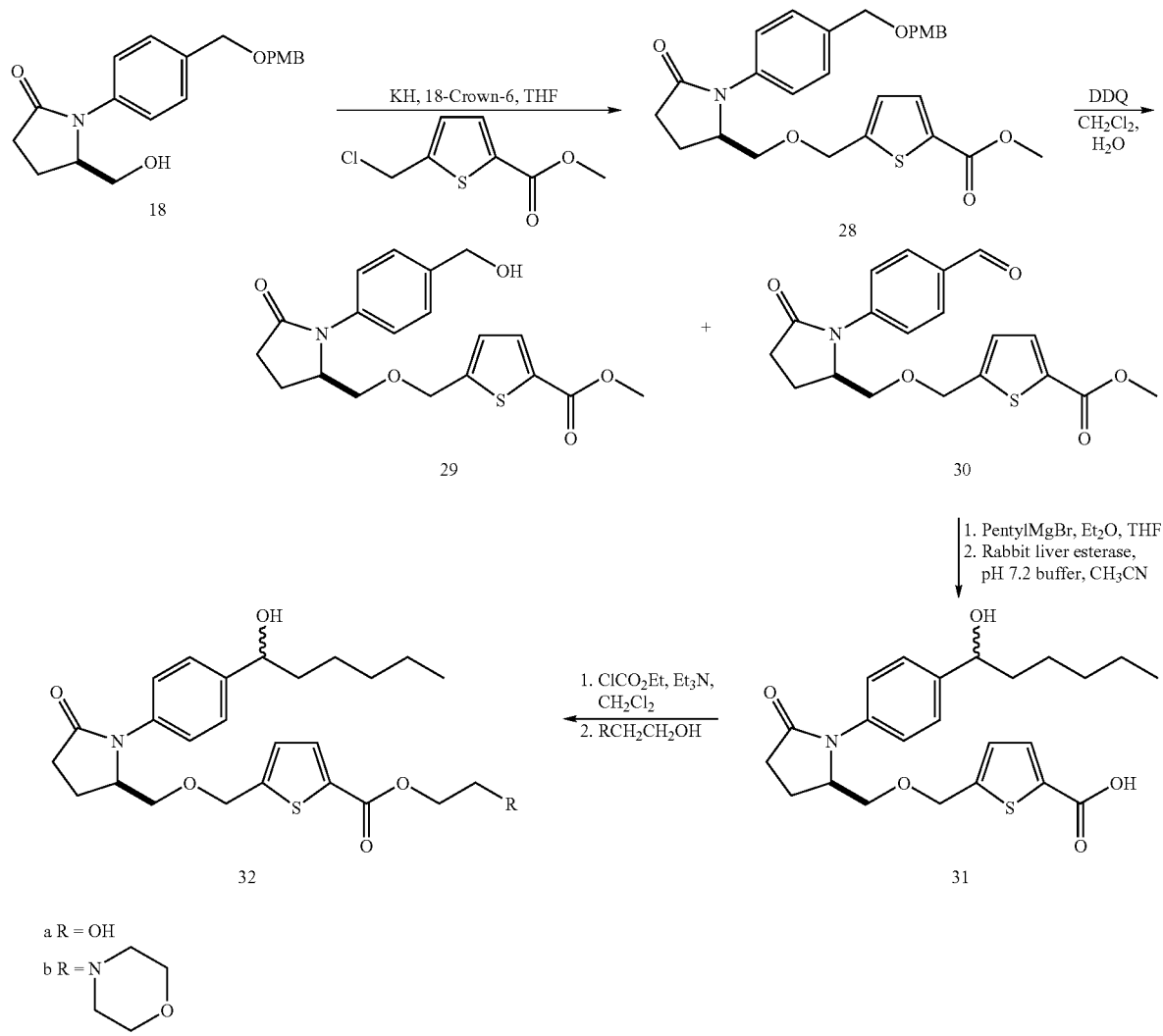

Step 2. Oxidative Deprotection of 28 to Give 29 and 30

DDQ (91 mg, 0.40 mmol) was added to a mixture of 28 (98 mg, 0.20 mmol) in CH$_2$Cl$_2$ (3 mL) and water (0.15 mL). After 4.5 h, the reaction was quenched with saturated aqueous NaHCO$_3$ (15 mL) and extracted with EtOAc (3×25 mL). Combined extracts were washed with brine (40 mL) then dried (Na$_2$SO$_4$), filtered and concentrated in vacuo. Purification of the residue by preparative thin layer chromatography (5% MeOH/CH$_2$Cl$_2$) afforded 14.4 mg (19%) of alcohol 29 and 16.2 mg (22%) of aldehyde 30.

Step 3. Grignard Reaction with 30 to Give the Ester of 31

Pentyl magnesium bromide (2.0 M in Et$_2$O, 22 μL, 0.044 mmol) was added to a solution of aldehyde 30 (11 mg, 0.029 mmol) in THF (0.2 mL) at −40° C. under nitrogen. After 1.5 h, the reaction was quenched with saturated aqueous NH$_4$Cl and extracted with CH$_2$Cl$_2$ (3×7 mL). Combined extracts were dried (Na$_2$SO$_4$), filtered and concentrated in vacuo. Purification of the residue by preparative thin layer chromatography (5% MeOH/CH$_2$Cl$_2$) afforded 4.8 mg (37%) of the desired ester.

Step 4. Saponification to Give 31

Rabbit liver esterase (134 units/mg, 1 mg) was added to a solution of the ester from step 3 above (3.6 mg, 0.008 mmol) in MeCN (0.1 mL) and pH 7.2 buffer (2.5 mL). After 16.5 h at rt, the reaction was diluted with MeCN (7 mL) and concentrated in vacuo. The residue was suspended in CH$_2$Cl$_2$ and filtered through a cotton plug. The filtrate was concentrated in vacuo to afford 2.0 mg (57%) of compound 31.

Step 5. Compounds 32a and 32b

Compounds 32a and 32b are prepared from compound 31 according to Example 1, step 5.

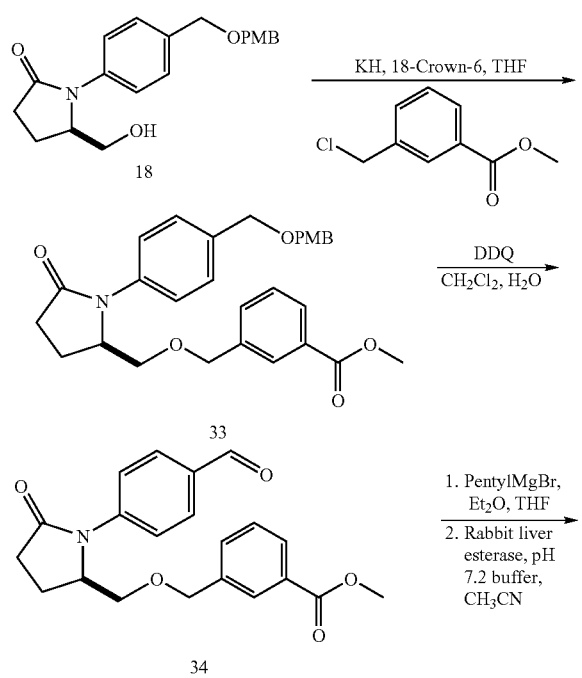

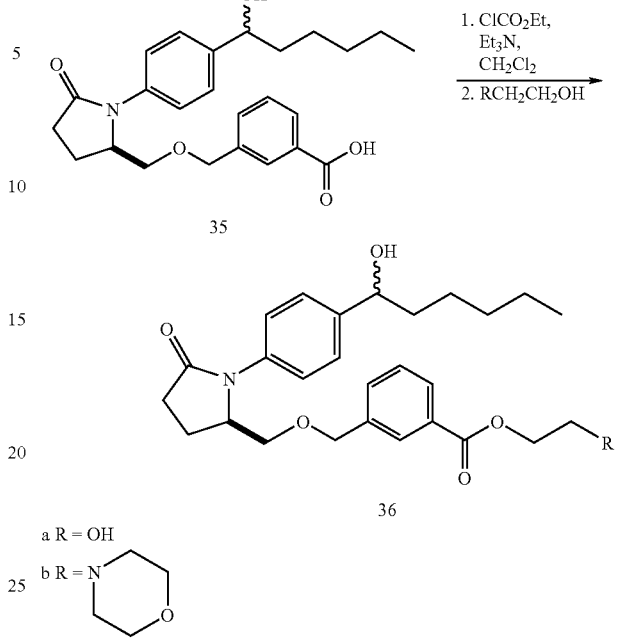

Example 10

Step 1. Alkylation of 18 to Give 33

Potassium hydride (16 mg, 0.39 mmol) was added to a solution of alcohol 18 (112 mg, 0.33 mmol) in THF (1.0 mL) at 0° C. After 1 h at 0° C., 18-crown-6 (114 mg, 0.43 mmol), potassium iodide (5 mg, 0.03 mmol) and a solution of methyl 3-chloromethylbenzoate (121 mg, 0.66 mmol) in THF (0.5 mL) were added sequentially. The reaction was allowed to warm to rt. After 19 h, the reaction was quenched with 0.1 N HCl (10 mL) and extracted with EtOAc (3×10 mL). Combined extracts were washed with brine (15 mL) then dried (Na$_2$SO$_4$), filtered and concentrated in vacuo. Purification of the residue by flash column chromatography on silica gel (20% EtOAc/Hexane→EtOAc, gradient) afforded 23 mg (14%) of desired product 33.

Step 2. Oxidative Deprotection of 33 to Give 34

DDQ (23 mg, 0.10 mmol) was added to a mixture of 33 (23 mg, 0.047 mmol) in CH$_2$Cl$_2$ and water (20:1, 0.25 mL). After 3.75 h, the reaction was quenched with saturated aqueous NaHCO$_3$ (10 mL) and extracted with EtOAc (3×7 mL). Combined extracts were washed with brine (10 mL) then dried (Na$_2$SO$_4$), filtered and concentrated in vacuo. Purification of the residue by preparative thin layer chromatography (80% EtOAc/Hex) afforded 13 mg (58%) of aldehyde 34.

Step 3. Grignard Reaction with 34 to Give the Ester of 35

Pentyl magnesium bromide (2.0 M in Et$_2$O, 50 μL, 0.10 mmol) was added to a solution of aldehyde 34 (12.4 mg, 0.034 mmol) in THF (0.1 mL) at −40° C. under nitrogen. After 1 h, the reaction was quenched with saturated aqueous NH$_4$Cl (7 mL) and extracted with CH$_2$Cl$_2$ (3×7 mL). Combined extracts were dried (Na$_2$SO$_4$), filtered and concentrated in vacuo.

Purification of the residue by preparative thin layer chromatography (5% MeOH/CH$_2$Cl$_2$) afforded 8.6 mg (58%) of the desired ester.

Step 4. Saponification to Give 35

Rabbit liver esterase (134 units/mg, 1 mg) was added to a solution of the ester from step 3 above (7.4 mg, 0.017 mmol) in MeCN (0.1 mL) and pH 7.2 buffer (2.5 mL). After 18 h at rt, the reaction was diluted with MeCN (7 mL) and concentrated in vacuo. Purification of the residue by preparative thin layer chromatography (5% MeOH/CH$_2$Cl$_2$) afforded 1.5 mg (21%) of compound 35.

Step 5. Compounds 36a and 36b

Compounds 36a and 36b are prepared from compound 35 according to Example 1, step 5.

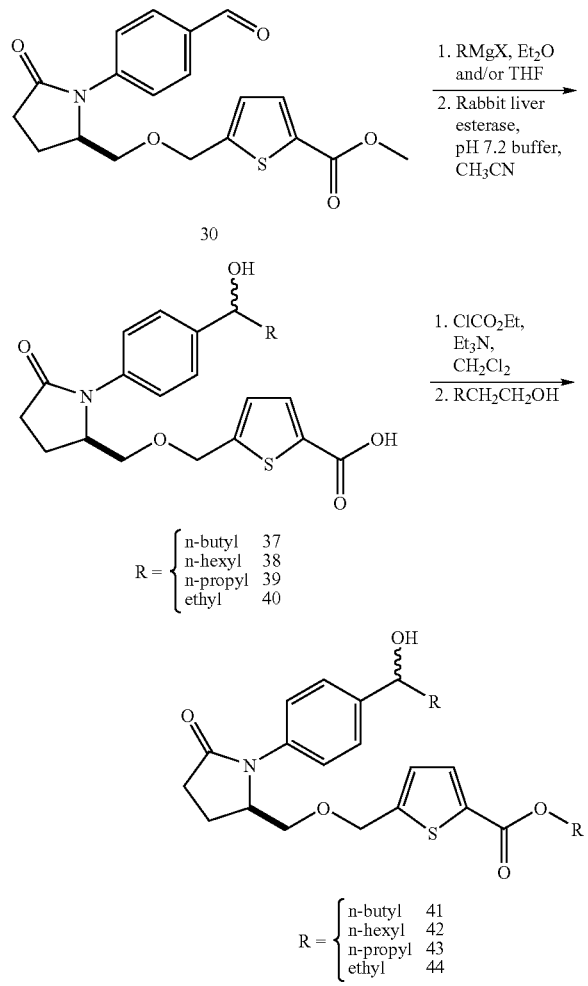

Scheme 6

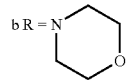

Example 11

Step 1. Grignard Reaction with 30 to Give the Ester of 37 n-Butyl magnesium chloride (2.0 M in THF, 41 µL, 0.082 mmol) was added to a solution of aldehyde 30 (20.2 mg, 0.054 mmol) in THF (0.1 mL) at −40° C. under nitrogen. After 1 h, the reaction was quenched with saturated aqueous NH$_4$Cl (10 mL) and extracted with CH$_2$Cl$_2$ (3×7 mL). Combined extracts were dried (Na$_2$SO$_4$), filtered and concentrated in vacuo. Purification of the residue by preparative thin layer chromatography (5% MeOH/CH$_2$Cl$_2$) afforded 12.3 mg (53%) of the desired ester.

Step 2. Saponification to Give 37

Rabbit liver esterase (134 units/mg, 1 mg) was added to a solution of the ester from step 1 above (11.2 mg, 0.026 mmol) in MeCN (0.1 mL) and pH 7.2 buffer (3.0 mL). After 19 h at rt, the reaction was diluted with MeCN (10 mL) and concentrated in vacuo. The residue was suspended in 5% MeOH/CH$_2$Cl$_2$ and filtered through a cotton plug. The filtrate was concentrated in vacuo to afford 10.7 mg (99%) of compound 37.

Step 3. Compounds 41a and 41b

Compounds 41a and 41b are prepared from compound 37 according to Example 1, step 5.

Example 12

Step 1. Grignard Reaction with 30 to Give the Ester of 38 n-Hexyl magnesium bromide (2.0 M in Et$_2$O, 100 L, 0.20 mmol) was added to a solution of aldehyde 30 (24.6 mg, 0.054 mmol) in THF (0.12 mL) at −40° C. under nitrogen. After 1.5 h, the reaction was quenched with saturated aqueous NH$_4$Cl (10 mL) and extracted with CH$_2$Cl$_2$ (3×7 mL). Combined extracts were dried (Na$_2$SO$_4$), filtered and concentrated in vacuo. Purification of the residue by preparative thin layer chromatography (5% MeOH/CH$_2$Cl$_2$) afforded 16.3 mg (54%) of the desired ester.

Step 2. Saponification to Give 38

Rabbit liver esterase (134 units/mg, 1 mg) was added to a solution of the ester from step 1 above (13 mg, 0.028 mmol) in MeCN (0.1 mL) and pH 7.2 buffer (3.0 mL). After 18 h at rt, the reaction was diluted with MeCN (10 mL) and concentrated in vacuo. The residue was suspended in 5% MeOH/CH$_2$Cl$_2$ and filtered through a cotton plug. The filtrate was concentrated in vacuo to afford 11 mg (87%) of compound 38.

Step 3. Compounds 42a and 42b

Compounds 42a and 42b are prepared from compound 38 according to Example 1, step 5.

Example 13

Step 1. Grignard Reaction with 30 to Give the Ester of 39 n-Propyl magnesium chloride (2.0 M in Et$_2$O, 92 µL, 0.18 mmol) was added to a solution of aldehyde 30 (22.9 mg, 0.061 mmol) in THF (0.12 mL) at −40° C. under nitrogen. After 1.75 h, the reaction was quenched with saturated aqueous NH$_4$Cl (10 mL) and extracted with CH$_2$Cl$_2$ (3×7 mL). Combined extracts were dried (Na$_2$SO$_4$), filtered and concentrated in vacuo. Purification of the residue by preparative thin layer chromatography (5% MeOH/CH$_2$Cl$_2$) afforded 13 mg (51%) of the desired ester.

Step 2. Saponification to Give 39

Rabbit liver esterase (134 units/mg, 1 mg) was added to a solution of the ester from step 1 above (10.8 mg, 0.026 mmol) in MeCN (0.1 mL) and pH 7.2 buffer (3.0 mL). After 17 h at rt, the reaction was diluted with MeCN (10 mL) and concentrated in vacuo. The residue was suspended in 5% MeOH/CH$_2$Cl$_2$ and filtered through a cotton plug. The filtrate was concentrated in vacuo to afford 10.4 mg (99%) of compound 39.

Step 3. Compounds 43a and 43b

Compounds 43a and 43b are prepared from compound 39 according to Example 1, step 5.

Example 14

Step 1. Grignard Reaction with 30 to Give the Ester of 40

Ethyl magnesium chloride (2.0 M in Et$_2$O, 24 µL, 0.048 mmol) was added to a solution of aldehyde 30 (5.8 mg, 0.016 mmol) in THF (0.1 mL) at −40° C. under nitrogen. After 1.25 h, the reaction was quenched with saturated aqueous NH$_4$Cl (5 mL) and extracted with CH$_2$Cl$_2$ (3×5 mL). Combined extracts were dried (Na$_2$SO$_4$), filtered and concentrated in vacuo. Purification of the residue by preparative thin layer chromatography (5% MeOH/CH$_2$Cl$_2$) afforded 2.5 mg (40%) of the desired ester.

Step 2. Saponification to Give 40

Rabbit liver esterase (134 units/mg, 1 mg) was added to a solution of the ester from step 1 above (2.8 mg, 0.007 mmol) in MeCN (0.1 mL) and pH 7.2 buffer (2.5 mL). After 17 h at rt, the reaction was diluted with MeCN (10 mL) and concentrated in vacuo. The residue was suspended in 5% MeOH/CH$_2$Cl$_2$ and filtered through a cotton plug. The filtrate was concentrated in vacuo to afford 2.7 mg (99%) of compound 40.

Step 3. Compounds 44a and 44b

Compounds 44a and 44b are prepared from compound 40 according to Example 1, step 5.

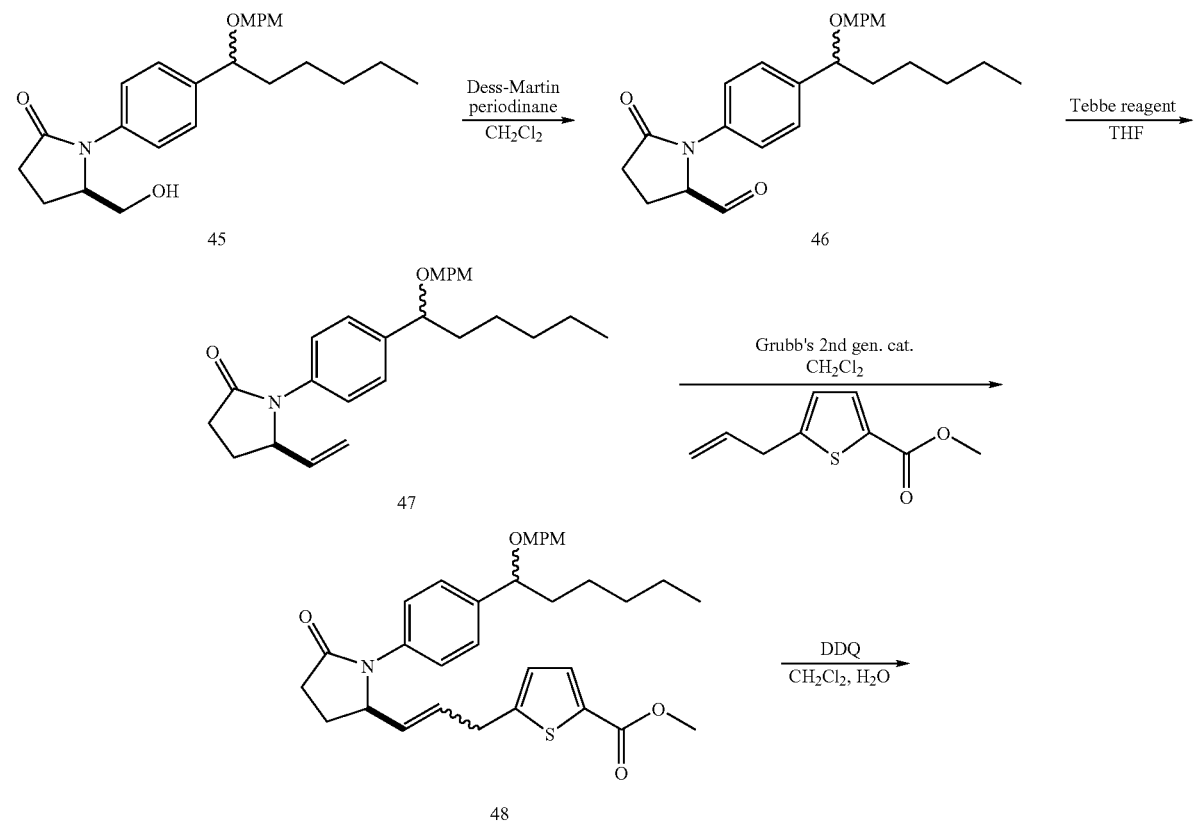

Scheme 7

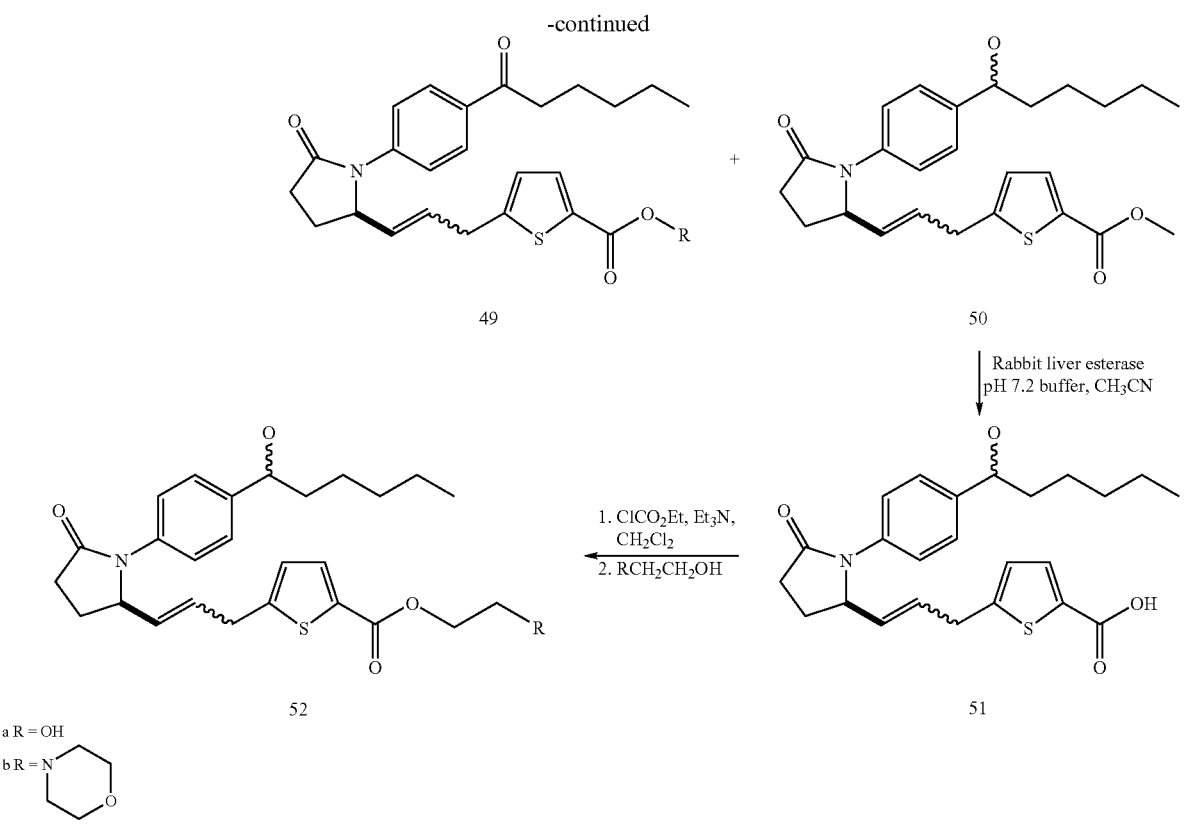

a R = OH
b R = N⟨morpholine⟩

Example 15

Step 1. Oxidation of 45 to Give Aldehyde 46

Dess-Martin periodinane (1.63 g, 3.83 mmol) was added to a solution of alcohol 45 (1.43 g, 3.48 mmol) in CH$_2$Cl$_2$ (12 mL) at rt under nitrogen. After 1 h at rt the reaction was quenched with saturated aqueous NaHCO$_3$ and saturated aqueous NaHSO$_3$ (1:1, 100 mL). The mixture was extracted with CH$_2$Cl$_2$ (3×150 mL). The combined extracts were dried (Na$_2$SO$_4$), filtered and concentrated in vacuo. Purification of the residue by flash column chromatography on silica (2% MeOH/CH$_2$Cl$_2$) afforded 915 mg (64%) of the desired aldehyde 46.

Step 2. Methylenation of 46 to Give Alkene 47

The Tebbe reagent (0.5 M in THF, 4.86 mL, 2.43 mmol) was added to a solution of aldehyde 46 (677 mg, 1.65 mmol) in THF (11 mL) at −40° C. under nitrogen. After 1 h at −40° C. the reaction was quenched by addition of aqueous 2 N NaOH (1.65 mL) and stirred vigorously overnight with the addition of THF (15 mL). The mixture was filtered through celite, washing with excess EtOAc. The filtrate was concentrated in vacuo. Purification of the residue by flash column chromatography on silica (30%→50% EtOAc/Hex) afforded 254 mg (38%) of the desired alkene 47.

Step 3. Metathesis Reaction of 47 to Give Alkene 48

Benzylidene[1,3-bis(2,4,6-trimethylphenyl)-2-imidazolidinylidene]dichloro(tricyclohexylphosphine)-ruthenium (Grubbs' catalyst, 2nd generation, 48 mg, 0.057 mmol) was added to a solution of alkene 47 (230 mg, 0.56 mmol) and methyl 5-allylthiophene-2-carboxylate (preparation 3, 206 mg, 1.13 mmol) in CH$_2$Cl$_2$ (3.0 mL). The reaction mixture was heated at reflux for 4 h. The reaction mixture was cooled to rt and more catalyst (48 mg, 0.057 mmol) and methyl 5-allylthiophene-2-carboxylate (100 mg, 0.55 mmol) were added. The mixture was heated for 18 h longer at reflux then cooled and concentrated in vacuo. Purification of the residue by flash column chromatography on silica (5%→50% EtOAc/Hex, gradient) afforded 100 mg (32%) of the desired alkene 48 along with 130 mg (57%) of the starting alkene 47.

Step 4. Oxidative Deprotection of 48 to Give 49 and 50

DDQ (58 mg, 0.26 mmol) was added to a mixture of 48 (130 mg, 0.23 mmol) in CH$_2$Cl$_2$ (3.1 mL) and water (0.16 mL) at 0° C. under nitrogen. After 45 min, the reaction was quenched with saturated aqueous NaHCO$_3$ (40 mL). The mixture was extracted with EtOAc (3×30 mL). The combined extracts were washed with brine (25 mL) then dried (Na$_2$SO$_4$), filtered and concentrated in vacuo. Purification of the residue by flash column chromatography on silica (50%→75% EtOAc/Hex, gradient) afforded 28 mg of an inseparable mixture of starting material 48 and ketone 49, and 63 mg (62%) of the desired alcohol 50.

Step 5. Saponification of 50 to Give 51

Rabbit liver esterase (134 units/mg, 1 mg) was added to a solution of ester 50 (3.7 mg, 0.008 mmol) in MeCN (0.2 mL) and pH 7.2 buffer (2.5 mL). After 15.5 h at rt, the reaction was diluted with MeCN (8 mL) and concentrated in vacuo. The residue was suspended in 10% MeOH/CH$_2$Cl$_2$ and filtered through a cotton plug. The filtrate was concentrated in vacuo to afford 3.0 mg (84%) of compound 51.

Step 6. Compounds 52a and 52b

Compounds 52a and 52b are prepared from compound 51 according to Example 1, step 5.

Example 16

Step 1. Oxidation of 38/39 Afford 39

DDQ (5.5 mg, 0.024 mmol) was added to the mixture of ether 48 and ketone 49 (6.8 mg, 0.012 mmol) in CH$_2$Cl$_2$ and water (20:1, 0.25 mL) at room temperature under nitrogen.

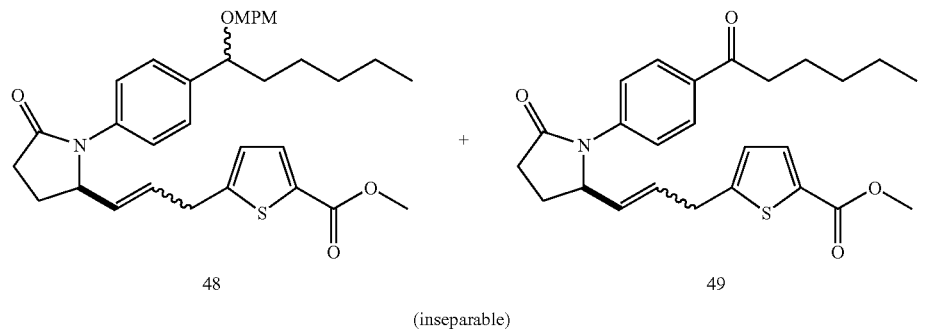

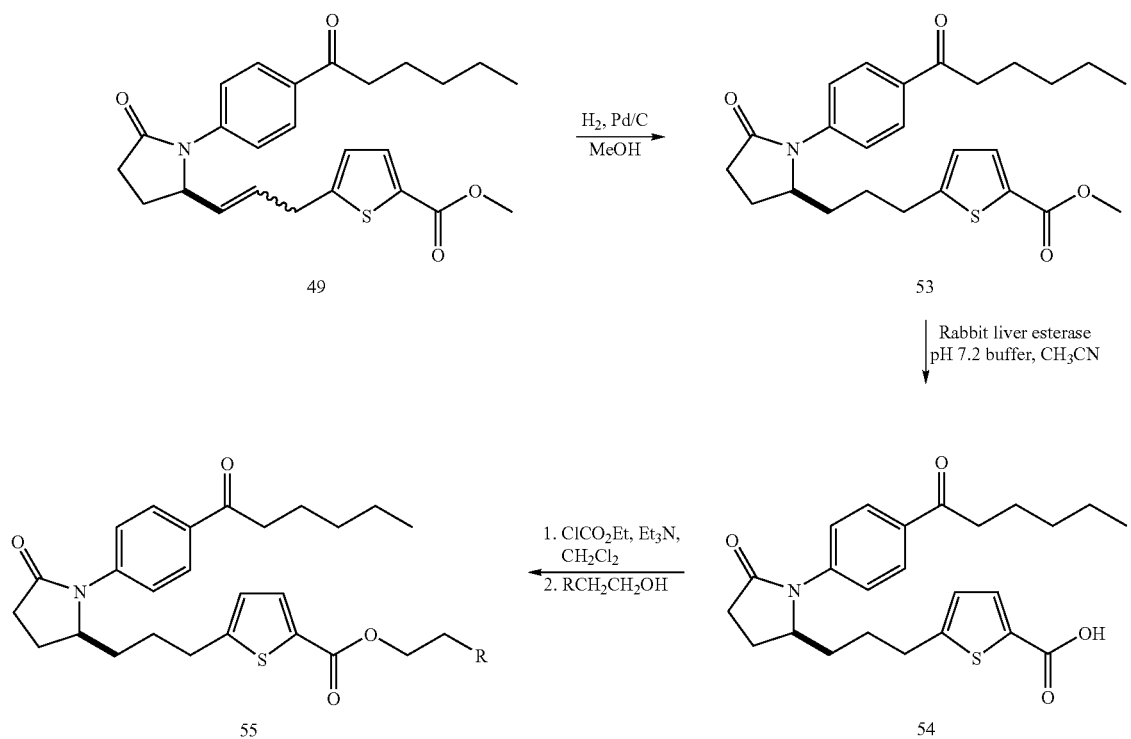

After 1.5 h, the reaction was quenched with saturated aqueous NaHCO$_3$ (5 mL). The mixture was extracted with EtOAc (3×5 mL). The combined extracts were washed with brine (5 mL) then dried (Na$_2$SO$_4$), filtered and concentrated in vacuoPurification of the residue by preparative thin layer chroma.

tography (60% EtOAc/Hex) afforded 1.5 mg (28%) of desired ketone 49.

Step 2. Hydrogenation of 49 to Give Ester 53

Palladium on carbon (10 wt. %, 1 mg) was added to a solution of alkene 49 (1.5 mg, 0.0034 mmol) in methanol (0.5 mL). A hydrogen atmosphere was established by evacuating and refilling with hydrogen (3×) and the reaction mixture was stirred under a balloon of hydrogen. After 2 h at rt, the reaction mixture was filtered through celite, washing with MeOH, and the filtrate was concentrated in vacuo to afford 1.3 mg (86%) of desired ester 53.

Step 3. Saponification of 53 to Give 54

Rabbit liver esterase (134 units/mg, 1 mg) was added to a solution of ester 53 (1.3 mg, 0.0029 mmol) in MeCN (0.1 mL) and pH 7.2 buffer (2.5 mL). After 23 h at rt, the reaction was diluted with MeCN (10 mL) and concentrated in vacuo. The residue was suspended in 10% MeOH/CH$_2$Cl$_2$ and filtered through a cotton plug. The filtrate was concentrated in vacuo to afford 1.2 mg (95%) of compound 54.

Step 4. Compounds 55a and 55b

Compounds 55a and 55b are prepared from compound 54 according to Example 1, step 5.

Scheme 9

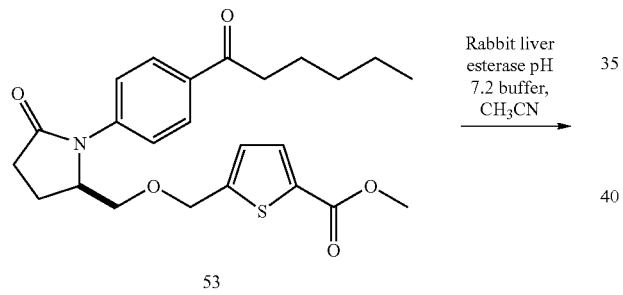

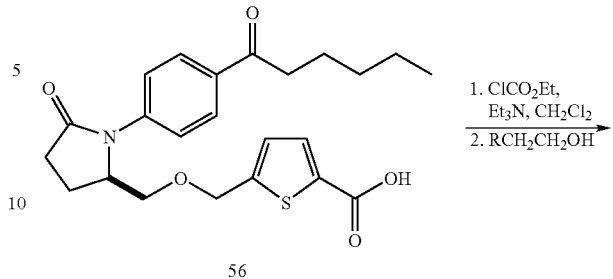

56

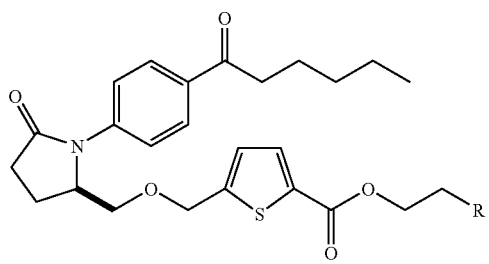

57 a R = OH b R = N⏝O (morpholine)

Example 17

Rabbit liver esterase (134 units/mg, 1 mg) was added to a solution of ester 53 (0.6 mg, 0.014 mmol) in MeCN (0.1 mL) and pH 7.2 buffer (2.5 mL). After 17 h at rt, the reaction was diluted with MeCN (8 mL) and concentrated in vacuo. Purification of the residue by preparative thin layer chromatography (4% MeOH/CH$_2$Cl$_2$) afforded 1 mg (17%) of compound 56. Compounds 57a and 57b are prepared from compound 56 according to Example 1, step 5.

Scheme 10

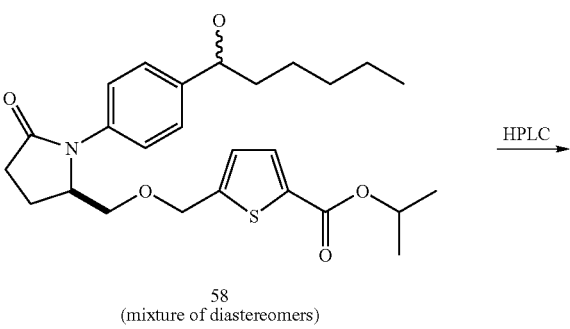

58
(mixture of diastereomers)

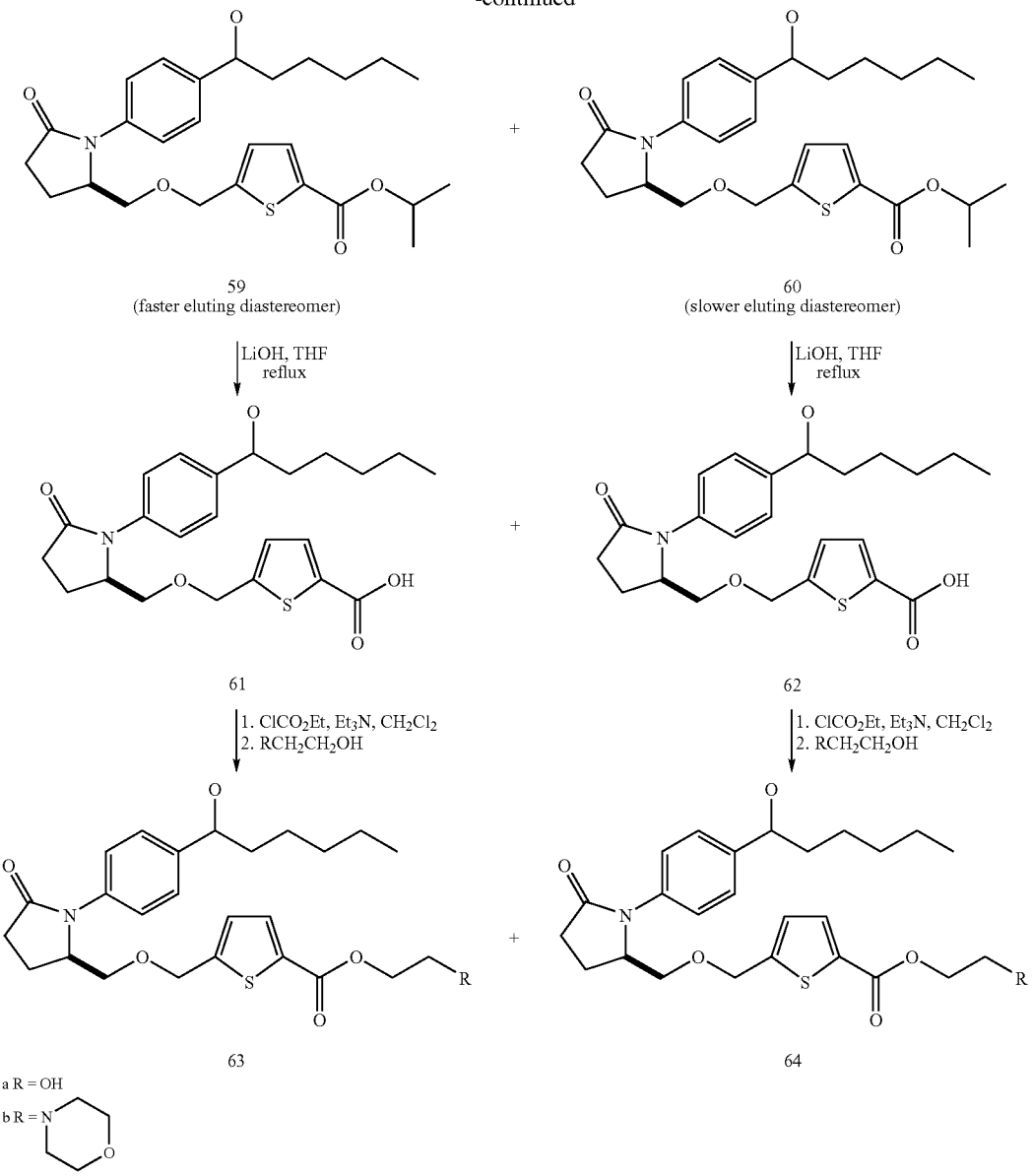

59 (faster eluting diastereomer)

60 (slower eluting diastereomer)

61

62

63

64 a R = OH
b R = N(morpholine)

Examples 18

The two diastereomers (58, ~100 mg) were separated on a Waters 600 HPLC instrument employing a Waters 2996 PDA detector and a Whatman Partisil® 10 M20/50 column, 22 mm×500 mm (Cat. No. 4232-220, Q.A. No. 3TA02D80). Using 60% EtOAc/Hex as the eluent and a flow rate of 15 mL/min, the first diastereomer (59, 32.8 mg total isolated) eluted at 55-60 min, and the second diastereomer (60, 52.6 mg total isolated) eluted at 61-70 min.

Example 19

Aqueous 1 N lithium hydroxide (0.05 mL, 0.05 mmol) was added to a solution of faster eluting ester diastereomer 59 (2.7 mg, 0.0057 mmol) in THF (0.1 mL) and the mixture was heated at reflux overnight. After 17 h, the reaction was cooled to rt, acidified with 0.05 N aqueous HCl (5 mL) and extracted with $CH_2Cl_2$ (3×5 mL). The combined extracts were dried ($Na_2SO_4$), filtered and concentrated in vacuo to afford 2.5 mg (100%) of compound 61. Compounds 63a and 63b are prepared from compound 61 according to Example 1, step 5.

Example 20

Aqueous 1 N lithium hydroxide (0.05 mL, 0.05 mmol) was added to a solution of slower eluting ester diastereomer 60 (2.8 mg, 0.0059 mmol) in THF (0.1 mL) and the mixture was heated at reflux overnight. After 23 h, the reaction was cooled to rt, acidified with 0.05 N aqueous HCl (5 mL) and extracted with $CH_2Cl_2$ (3×5 mL). The combined extracts were dried ($Na_2SO_4$), filtered and concentrated in vacuo to afford 1.7 mg (67%) of compound 62. Compounds 64a and 64b are prepared from compound 62 according to Example 1, step 5.

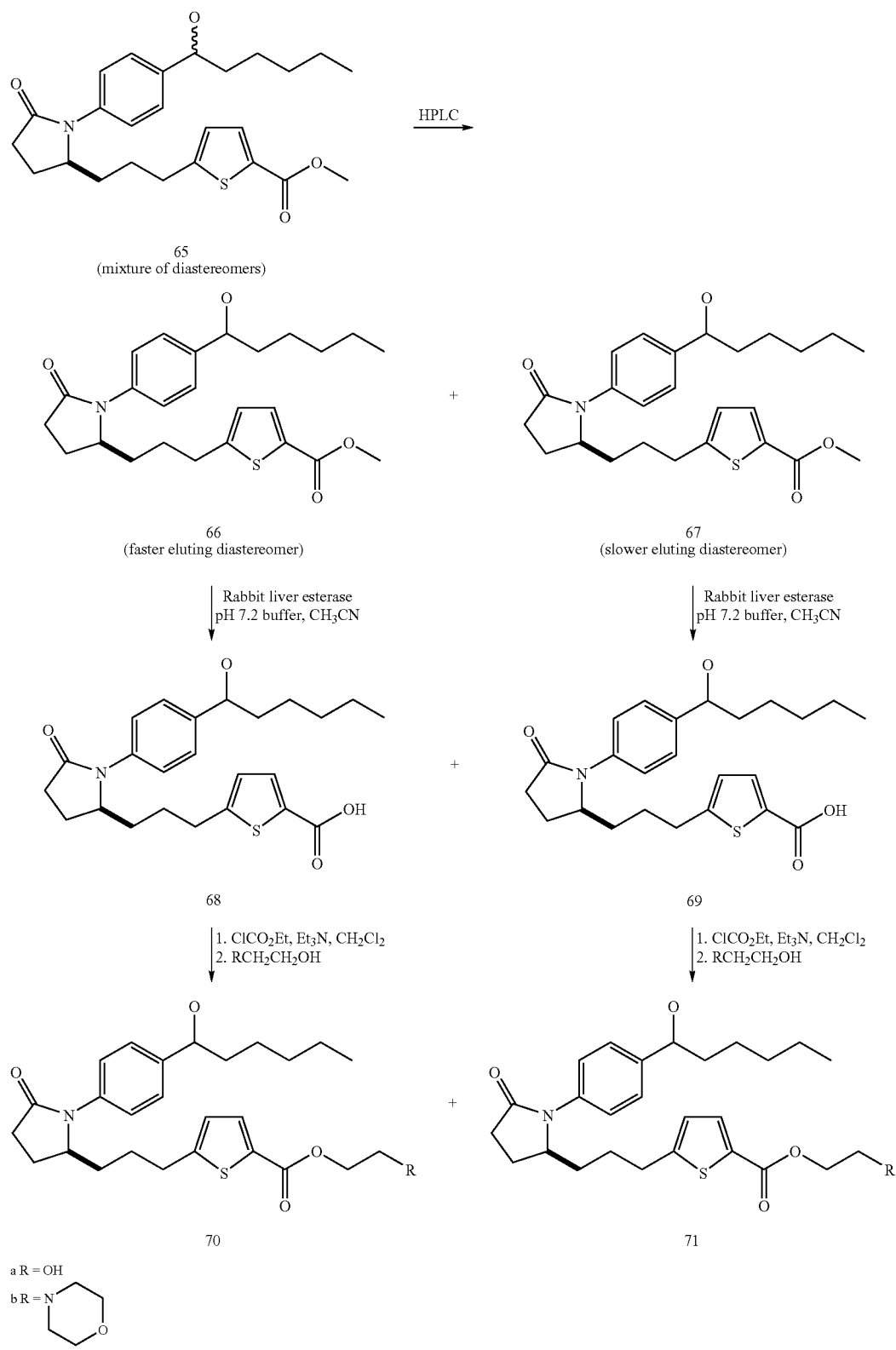
Scheme 11
65
(mixture of diastereomers)
66
(faster eluting diastereomer)
67
(slower eluting diastereomer)
68
69
70
71
a R = OH
b R = N(morpholine)

Examples 21

The two diastereomers (65, ~43 mg) were separated on a Waters 600 HPLC instrument employing a Waters 2996 PDA detector and a Whatman Partisil® 10 M20/50 column, 22 mm×500 mm (Cat. No. 4232-220, Q.A. No. 3TA02D80). Using 55% EtOAc/Hex as the eluent and a flow rate of 15 mL/min, the first diastereomer (66, 16 mg) eluted at 69-75 min, and the second diastereomer (67, 19 mg) eluted at 80-88 min.

Example 22

Rabbit liver esterase (134 units/mg, 2 mg) was added to a solution of faster eluting ester diastereomer 66 (16 mg, 0.036 mmol) in MeCN (0.2 mL) and pH 7.2 buffer (3.0 mL). After 18 h at rt, the reaction was diluted with MeCN (10 mL) and concentrated in vacuo. The residue was diluted with $CH_2Cl_2$ (5 mL), filtered through a plug of glass wool and concentrated in vacuo. Purification of the residue by preparative thin layer chromatography (EtOAc→25% MeOH/EtOAc, gradient) afforded 12 mg (77%) of compound 68. Compounds 70a and 70b are prepared from compound 68 according to Example 1, step 5.

Example 23

Rabbit liver esterase (134 units/mg, 2 mg) was added to a solution of slower eluting ester diastereomer 67 (19 mg, 0.043 mmol) in MeCN (0.2 mL) and pH 7.2 buffer (3.0 mL). After 18 h at rt, the reaction was diluted with MeCN (10 mL) and concentrated in vacuo. The residue was diluted with $CH_2Cl_2$ (5 mL), filtered through a plug of glass wool and concentrated in vacuo. Purification of the residue by preparative thin layer chromatography (EtOAc→25% MeOH/EtOAc, gradient) afforded 10.5 mg (57%) of compound 69. Compounds 71a and 71b are prepared from compound 69 according to Example 1, step 5.

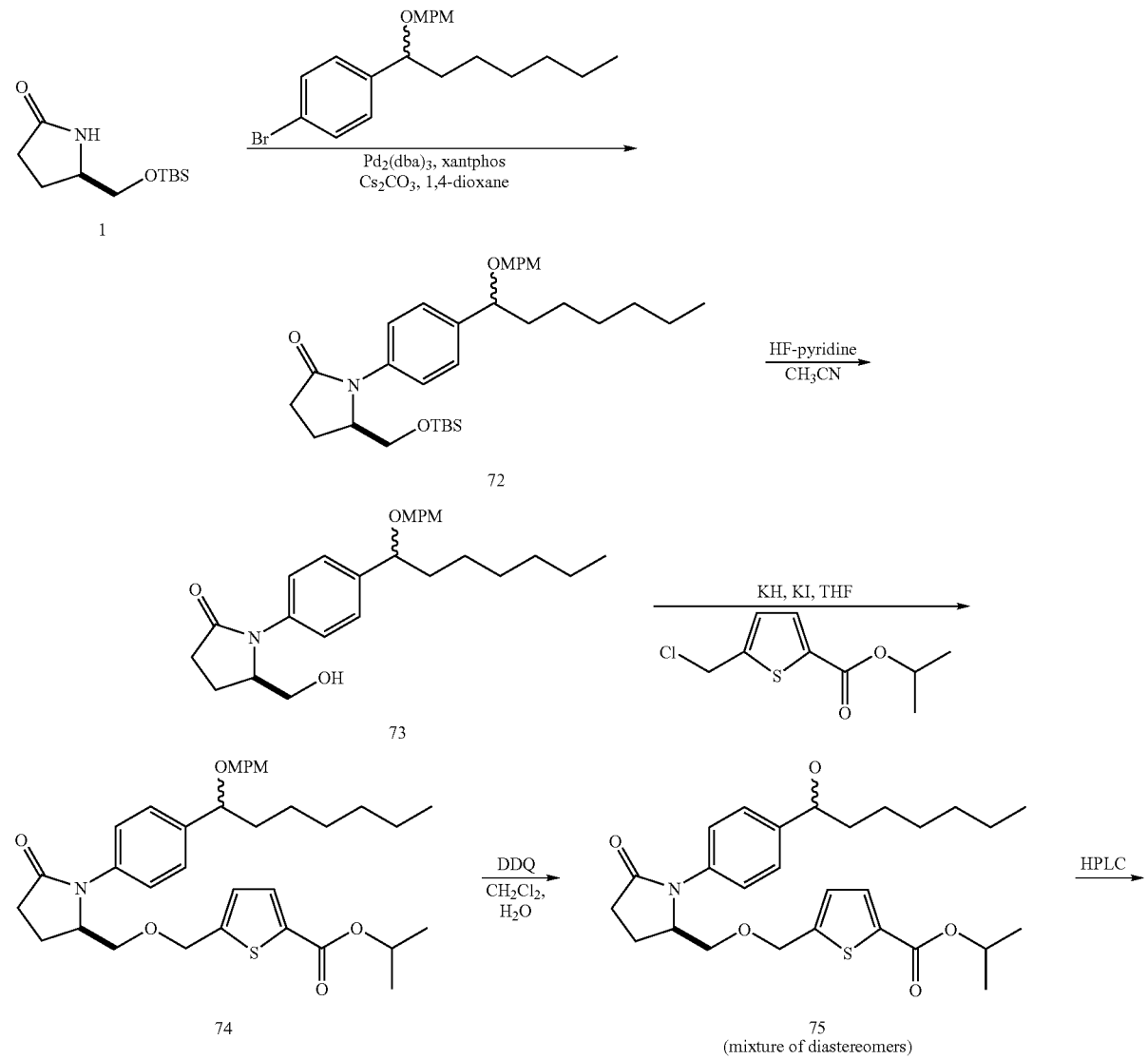

Scheme 12

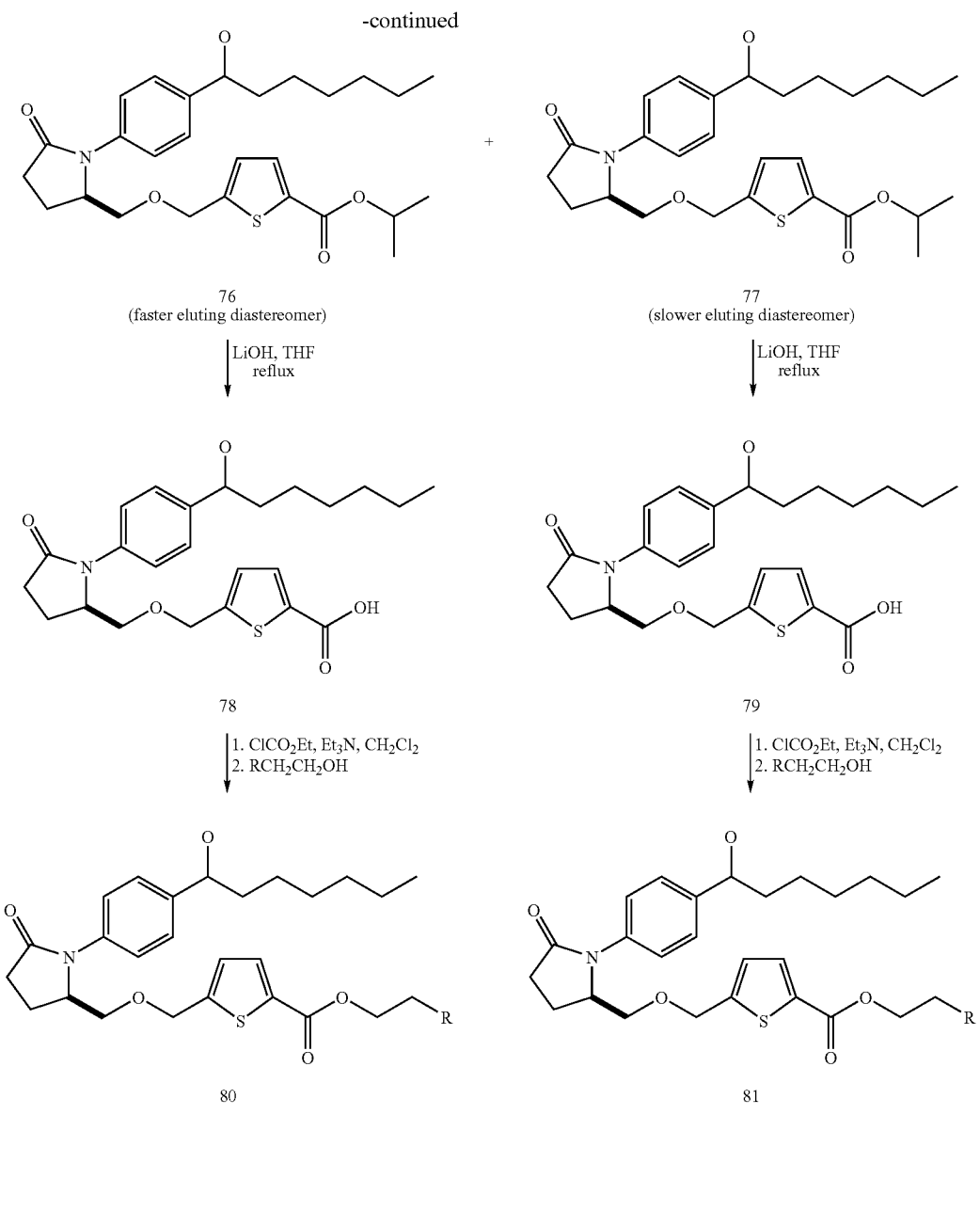

76 (faster eluting diastereomer)

77 (slower eluting diastereomer)

a R = OH
b R = N(morpholine)

Example 24

Step 1. Arylation of 1 to Give 72

Pd$_2$(dba)$_3$ (550 mg, 0.60 mmol), xantphos (1.04 g, 180 mmol) and Cs$_2$CO$_3$ g, 18.0 mmol) were added sequentially to a solution of amide 1 (3.45 g, 15.0 mmol) in 1,4-dioxane (100 mL). A solution of 1-(1-(4-methoxybenzyloxyheptyl)-4-bromobenzene (preparation 4, 5.30 g, 13.54 mmol) in 1,4-dioxane (50 mL) was added via cannula. The reaction mixture was purged with nitrogen then heated at reflux overnight. After 17 h, the reaction was cooled to rt and filtered through celite, washing with CH$_2$Cl$_2$. The filtrate was concentrated in vacuo and the residue was purified by flash column chromatography on silica gel (5%→35% EtOAc/Hexane, gradient) to afford 5.26 g (72%) of the desired product 72.

Step 2. Deprotection of 72 to Give 73

HF-pyridine (8.8 mL) was added to a solution of silyl ether 72 (5.26 g, 9.74 mmol) in MeCN (50 mL) in a plastic bottle at 0° C. After 45 min at 0° C., the reaction was quenched with saturated aqueous NaHCO$_3$ (400 mL). The mixture was extracted with EtOAc (3×200 mL). The combined extracts were washed with brine (200 mL) then dried (Na$_2$SO$_4$), filtered and concentrated in vacuo. Purification of the residue by flash column chromatography on silica (CH$_2$Cl$_2$→5% MeOH/CH$_2$Cl$_2$, gradient) afforded 3.9 g (94%) of the desired alcohol 73 as a pale yellow solid.

Step 3. Alkylation of 73 to Give 74

A round bottom flask was charged with potassium hydride (30 wt % in oil, 138 mg, 1.03 mmol). The material was washed with hexanes (3×1 mL), then suspended in THF (1 mL). The mixture was cooled to 0° C. and a solution of alcohol 73 (339 mg, 0.80 mmol) in THF (1.5 mL) was added via cannula. After 1 h at 0° C., a solution of isopropyl 5-chloromethylthiophene-2-carboxylate (preparation 2, 174 mg, 0.80 mmol) in THF (1.5 mL) was added via cannula. Potassium iodide (14 mg, 0.08 mmol) was added and the reaction was allowed to warm to rt. After 18 h, the reaction was quenched with saturated aqueous $NH_4Cl$ (15 mL) and extracted with EtOAc (3×25 mL). Combined extracts were washed with brine (15 mL) then dried ($Na_2SO_4$), filtered and concentrated in vacuo. Purification of the residue by flash column chromatography on silica gel (20%→75% EtOAc/Hexane, gradient), followed by preparative thin layer chromatography (65% EtOAc/Hexane) afforded 65 mg (14%) of desired product 74.

Step 4. Oxidative Deprotection of 74 to Give 75

DDQ (26 mg, 0.12 mmol) was added to a solution of 74 (65 mg, 0.11 mmol) in $CH_2Cl_2$ (1.4 mL) and water (0.07 mL) at 0° C. under nitrogen. After 40 min, the reaction was quenched with saturated aqueous $NaHCO_3$ (20 mL) and extracted with EtOAc (3×20 mL). Combined extracts were washed with brine (15 mL) then dried ($Na_2SO_4$), filtered and concentrated in vacuo. Purification of the residue by flash column chromatography on silica gel (50%→75% EtOAc/Hexane, gradient), followed by preparative thin layer chromatography (60% EtOAc/Hexane) afforded 36 mg (69%) of compound 75.

Examples 25

The two diastereomers (75, ~36 mg) were separated on a Waters 600 HPLC instrument employing a Waters 2996 PDA detector and a Whatman Partisil® 10 M20/50 column, 22 mm×500 mm (Cat. No. 4232-220, Q.A. No. 3TA02D80). Using 60% EtOAc/Hex as the eluent and a flow rate of 15 mL/min, the first diastereomer (76, 14.8 mg) eluted at 50-56.5 min, and the second diastereomer (77, 16.4 mg) eluted at 56.5-70 min.

Example 26

Aqueous 1 N lithium hydroxide (0.05 mL, 0.05 mmol) was added to a solution of faster eluting ester diastereomer 76 (3.5 mg, 0.0072 mmol) in THF (0.1 mL) and the mixture was heated at reflux overnight. After 18 h, the reaction was cooled to rt, diluted with water (2 mL), acidified with 1.0 N aqueous HCl (1 mL) and extracted with EtOAc (3×5 mL). The combined extracts were washed with brine (5 mL), dried ($Na_2SO_4$), filtered and concentrated in vacuo to afford 3.0 mg (94%) of compound 78. Compounds 80a and 80b are prepared from compound 78 according to Example 1, step 5.

Example 27

Aqueous 1 N lithium hydroxide (0.05 mL, 0.05 mmol) was added to a solution of slower eluting ester diastereomer 77 (3.5 mg, 0.0072 mmol) in THF (0.1 mL) and the mixture was heated at reflux overnight. After 18 h, the reaction was cooled to rt, diluted with water (2 mL), acidified with 1.0 N aqueous HCl (1 mL) and extracted with EtOAc (3×5 mL). The combined extracts were washed with brine (5 mL), dried ($Na_2SO_4$), filtered and concentrated in vacuo to afford 3.2 mg (99%) of compound 79. Compounds 81a and 81b are prepared from compound 79 according to Example 1, step 5.

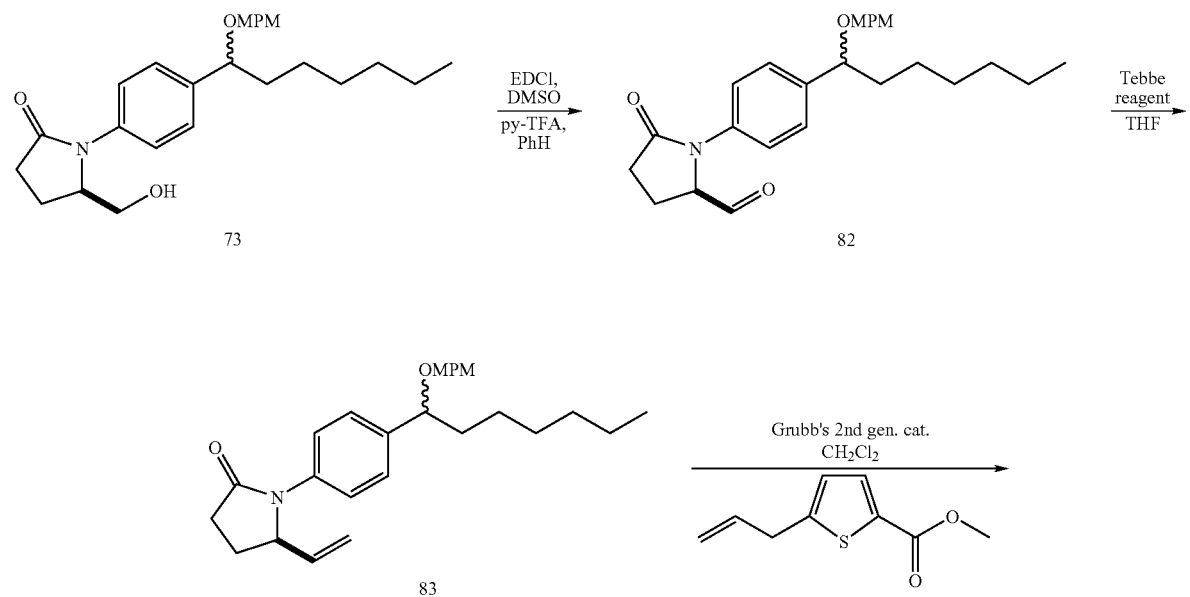

Scheme 13

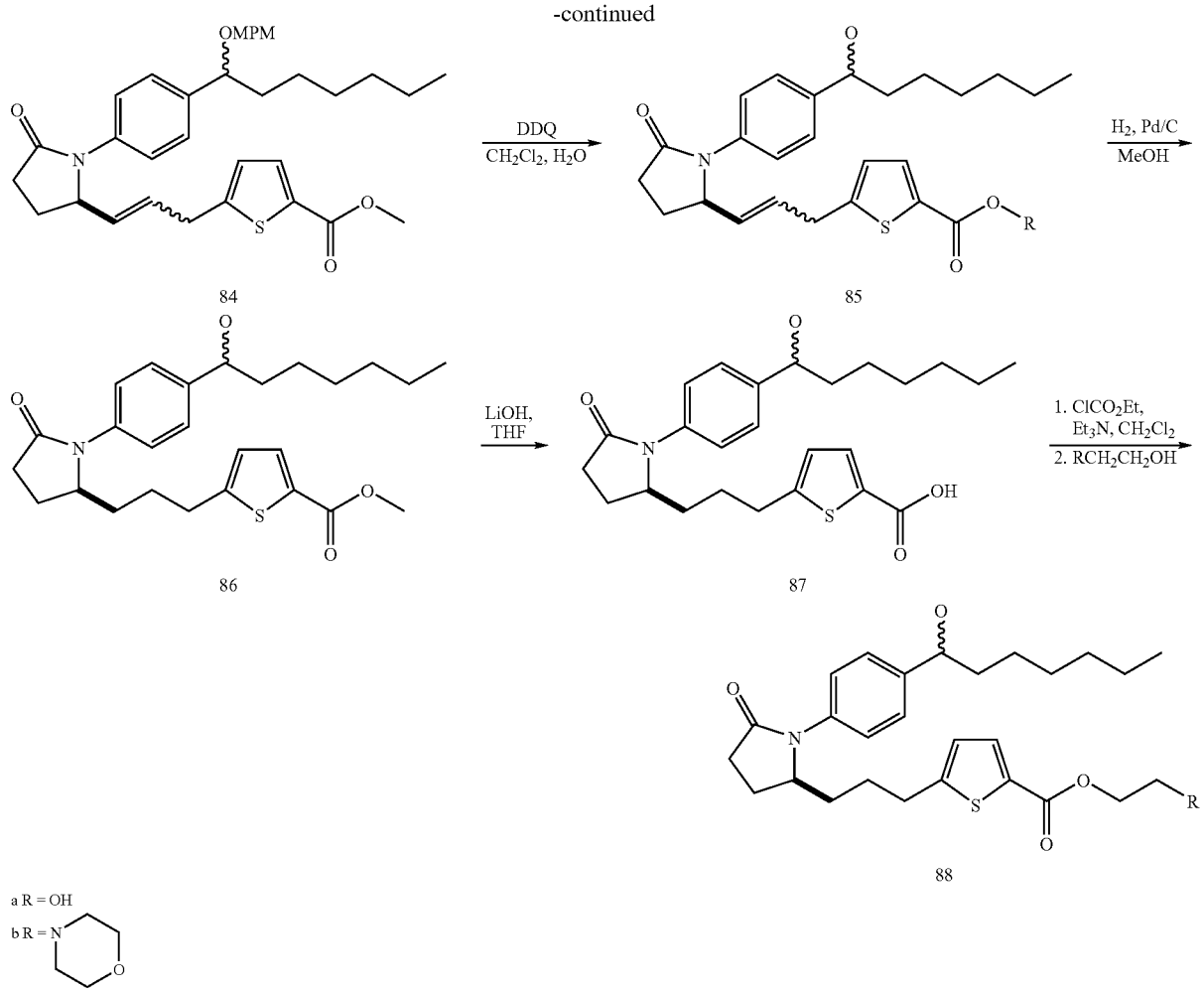

a R = OH b R = 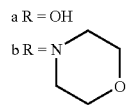

Example 28

Step 1. Oxidation of 73 to Give Aldehyde 82

1-(3-(Dimethylaminopropyl)-3-ethylcarbodiimide hydrochloride (EDCI, 1.43 g, 7.45 mmol) and DMSO (0.70 mL, 9.86 mmol) were added sequentially to a solution of alcohol 73 (1.06 g, 2.48 mmol) in benzene (25 mL) at rt under nitrogen. After 10 min at rt, pyridinium trifluoroacetate (527 mg, 2.73 mmol) was added. After 3 h at rt, the solution was decanted from the oily residue and the residue was washed with benzene (3×15 mL). The combined benzene phases were concentrated in vacuo. Purification of the residue by flash column chromatography on silica ($CH_2Cl_2 \rightarrow 3\%$ MeOH/$CH_2Cl_2$, gradient) afforded 1.0 g (95%) of the desired aldehyde 82.

Step 2. Methylenation of 82 to Give Alkene 83

The Tebbe reagent (0.5 M in THF, 7.0 mL, 3.5 mmol) was added to a solution of aldehyde 82 (1.0 g, 2.36 mmol) in THF (16 mL) at −40° C. under nitrogen. After 1 h at −40° C. the reaction was quenched by addition of aqueous 2 N NaOH (5.25 mL) and stirred vigorously overnight with the addition of THF (20 mL). The mixture was filtered through celite, washing with excess EtOAc. The filtrate was concentrated in vacuo. Purification of the residue by flash column chromatography on silica (40% EtOAc/Hex) afforded 195 mg (20%) of the desired alkene 83.

Step 3. Metathesis Reaction of 83 to Give Alkene 84

Grubbs' second generation catalyst (38 mg, 0.045 mmol) was added to a solution of alkene 83 (190 mg, 0.45 mmol) and methyl 5-allylthiophene-2-carboxylate (preparation 3, 173 mg, 0.95 mmol) in $CH_2Cl_2$ (2.4 mL). The reaction mixture was heated at reflux for 2 h. The reaction mixture was cooled to rt and more catalyst (9 mg, 0.011 mmol) and methyl 5-allylthiophene-2-carboxylate (165 mg, 0.91 mmol) were added. The mixture was heated for 22 h longer at reflux then cooled and concentrated in vacuo. Purification of the residue by flash column chromatography on silica (2 times, first using 5%→50% EtOAc/Hex, gradient then second using $CH_2Cl_2 \rightarrow 3\%$ MeOH/$CH_2Cl_2$, gradient) afforded 180 mg (69%) of the desired alkene 84.

Step 4. Oxidative Deprotection of 84 to Give 85

DDQ (78 mg, 0.34 mmol) was added to a mixture of 84 (180 mg, 0.31 mmol) in $CH_2Cl_2$ (4.1 mL) and water (0.21 mL) at 0° C. under nitrogen. After 45 min at 0° C., the reaction was quenched with saturated aqueous $NaHCO_3$ (50 mL). The mixture was extracted with EtOAc (3×50 mL). The combined extracts were washed with brine (50 mL) then dried (Na$_2$SO$_4$), filtered and concentrated in vacuo. Purification of the residue by flash column chromatography on silica (50%→66% EtOAc/Hex, gradient) afforded 50 mg (35%) of the desired alcohol 85.

Step 5. Hydrogenation of 85 to Give Ester 86

Palladium on carbon (10 wt. %, 12 mg) was added to a solution of alkene 85 (50 mg, 0.11 mmol) in methanol (2.3 mL). A hydrogen atmosphere was established by evacuating and refilling with hydrogen (3×) and the reaction mixture was stirred under a balloon of hydrogen. After 20 h at rt, the reaction mixture was filtered through celite, washing with MeOH, and the filtrate was concentrated in vacuo to afford 50 mg (99%) of the desired ester 86.

Step 6. Saponification of 86 to Give 87

Aqueous 1 N lithium hydroxide (0.19 mL, 0.19 mmol) was added to a solution of ester 86 (17 mg, 0.038 mmol) in THF (0.4 mL). After 18 h at rt, H$_2$O (1.0 mL) was added and the mixture was acidified with 1 N aqueous HCl (1.0 mL) and extracted with EtOAc (3×10 mL). The combined extracts were washed with brine (10 mL) then dried (Na$_2$SO$_4$), filtered and concentrated in vacuo. Purification of the residue by preparative thin layer chromatography (15% MeOH/CH$_2$Cl$_2$) afforded 5.6 mg (34%) of compound 87.

Step 7. Compounds 88a and 88b

Compounds 88a and 88b are prepared from compound 87 according to Example 1, step 5.

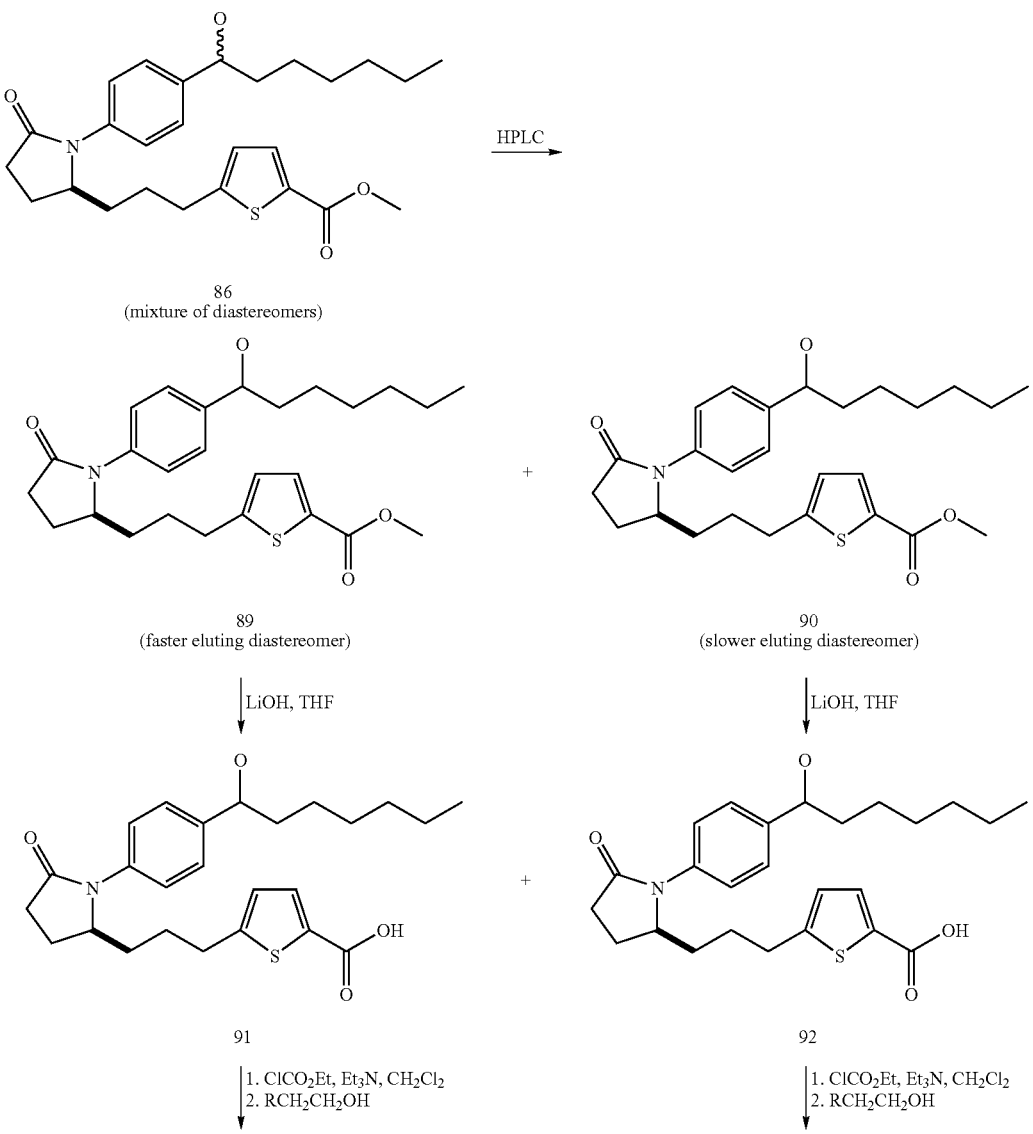

Scheme 14

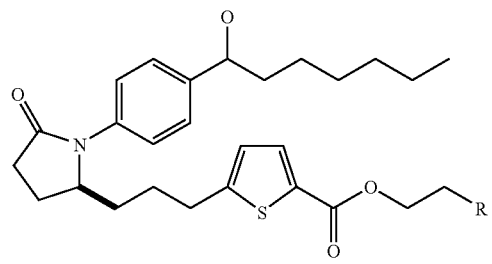
93

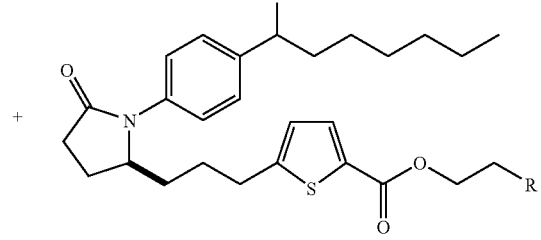
94 a R = OH
b R = 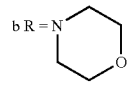

Examples 29

The two diastereomers 86 (~34 mg) were separated on a Waters 600 HPLC instrument employing a Waters 2996 PDA detector and a Whatman Partisil® 10 M20/50 column, 22 mm×500 mm (Cat. No. 4232-220, Q.A. No. 3TA02D80). Using 55% EtOAc/Hex as the eluent and a flow rate of 15 mL/min, the first diastereomer (89, 10.7 mg) eluted at 78-87.5 min, and the second diastereomer (90, 7.0 mg) eluted at 91-101 min.

Example 30

Aqueous 1 N lithium hydroxide (0.12 mL, 0.12 mmol) was added to a solution of faster eluting ester diastereomer 89 (10.7 mg, 0.023 mmol) in THF (0.3 mL). After 66 h at rt, $H_2O$ (1.0 mL) was added and the mixture was acidified with 1 N aqueous HCl (1.0 mL) and extracted with EtOAc (3×10 mL). The combined extracts were washed with brine (5 mL) then dried ($Na_2SO_4$), filtered and concentrated in vacuo to afford 10 mg (96%) of compound 91. Compounds 93a and 93b are prepared from compound 91 according to Example 1, step 5.

Example 31

Aqueous 1 N lithium hydroxide (0.08 mL, 0.08 mmol) was added to a solution of slower eluting ester diastereomer 90 (7.0 mg, 0.015 mmol) in THF (0.2 mL). After 66 h at rt, $H_2O$ (1.0 mL) was added and the mixture was acidified with 1 N aqueous HCl (1.0 mL) and extracted with EtOAc (3×8 mL). The combined extracts were washed with brine (5 mL) then dried ($Na_2SO_4$), filtered and concentrated in vacuo to afford 6.5 mg (96%) of compound 92. Compounds 94a and 94b are prepared from compound 92 according to Example 1, step 5.

Scheme 14

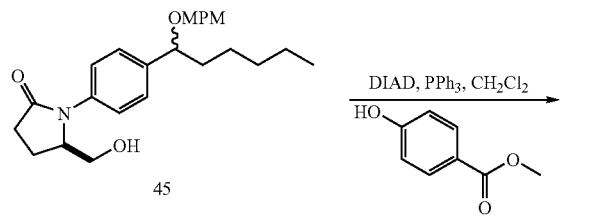
45

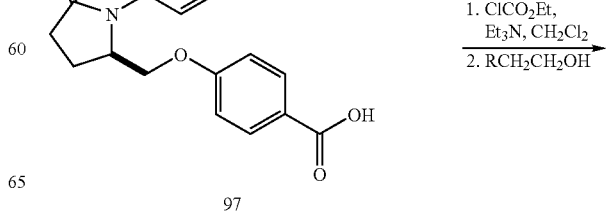

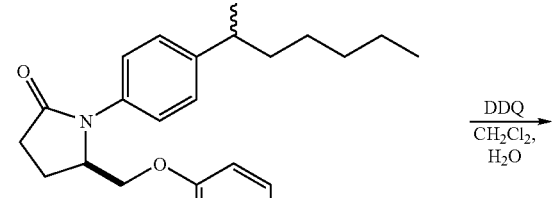
95

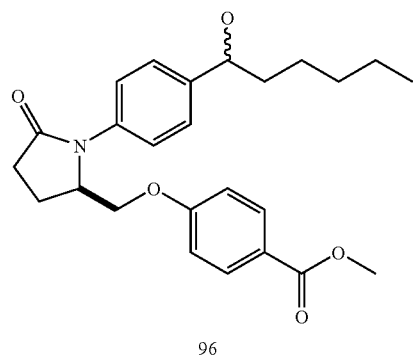
96

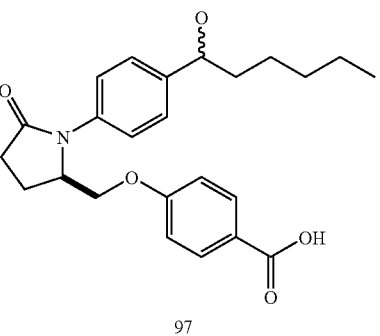
97

-continued

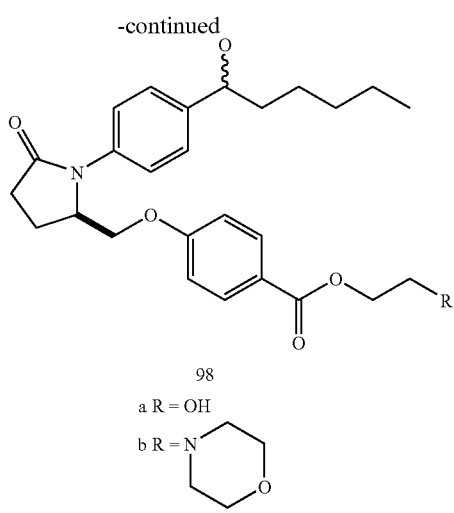

98
a R = OH
b R = N⏜O (morpholine)

Example 32

Step 1. Mitsunobu Reaction of 45 and Methyl 4-Hydroxybenzoate to Give 95

Diisopropyl azodicarboxylate (DIAD, 194 µL, 1.0 mmol) was added to a solution of alcohol 45 (200 mg, 0.49 mmol), triphenylphosphine (191 mg, 0.73 mmol) and methyl 4-hydroxybenzoate (87 mg, 0.57 mmol) in $CH_2Cl_2$ (2.5 mL). After stirring 18 h at rt, the solvent was removed under a stream of nitrogen and the residue was suspended in EtOAc (75 mL). The mixture was washed with saturated aqueous $NaHCO_3$ (3×25 mL) and brine (25 mL) then the organic phase was dried ($Na_2SO_4$) filtered and concentrated in vacuo. Purification of the residue by flash column chromatography on silica gel (50% EtOAc/hexane→EtOAc, gradient) afforded 81 mg (31%) of the desired ether 95.

Step 2. Oxidative Deprotection of 95 to Give 96

DDQ (37 mg, 0.16 mmol) was added to a mixture of 95 (81 mg, 0.15 mmol) in $CH_2Cl_2$ (2.0 mL) and water (0.1 mL) at 0° C. under nitrogen. After 45 min at 0° C., the was quenched with saturated aqueous $NaHCO_3$ (25 mL). The mixture was extracted with EtOAc (3×25 mL). The combined extracts were washed with brine (25 mL) then dried ($Na_2SO_4$), filtered and concentrated in vacuo. Purification of the residue by flash column chromatography on silica (85% EtOAc/Hex→EtOAc, gradient) afforded 31 mg (49%) of the desired alcohol 96.

Step 3. Saponification of 96 to Give 97

Aqueous 1 N lithium hydroxide (0.35 mL, 0.35 mmol) was added to a solution of ester 96 (30 mg, 0.071 mmol) in THF (0.7 mL). After 20 h at rt, water (2.0 mL) was added and the mixture was acidified with 1 N aqueous HCl (1.5 mL) and extracted with EtOAc (3×10 mL). The combined extracts were washed with brine (10 mL) then dried ($Na_2SO_4$), filtered and concentrated in vacuo. Purification of the residue by flash column chromatography on silica (EtOAc→10% MeOH/EtOAc, gradient) afforded 11.5 mg (38%) of starting ester 96 and 8.5 mg (29%) of compound 97.

Step 4. Compounds 98a and 98b

Compounds 98a and 98b are prepared from compound 97 according to Example 1, step 5.

Preparation 1

1-(1-(4-Methoxybenzyloxy-hexyl)-4-bromobenzene

Step 1. Pentyl Grignard Addition to 4-Bromobenzaldehyde n-Pentyl magnesium bromide (2.0 M in THF, 27 mL, 54 mmol) was added to a solution of 4-bromobenzaldehyde (5.0 g, 27 mmol) in THF (20 mL) at 0° C. under nitrogen. After 1 h, the reaction was quenched with 3 N HCl and extracted with $Et_2O$ (3×120 mL). Combined extracts were washed with brine (100 mL), dried ($Na_2SO_4$), filtered and concentrated in vacuo. Purification of the residue by flash column chromatography on silica gel (5% EtOAc/Hex) afforded 5.1 g (74%) of 1-(4-bromophenyl)-hexan-1-ol.

Step 2. Protection of the Alcohol as its MPM Ether

Sodium hydride (60% wt. in oil, 0.95 g, 23.8 mmol) was added to a solution of the alcohol from step 1 (5.11 g, 19.9 mmol) in THF and DMF (2:1, 20 mL) at 0° C. under nitrogen. After 1 h at 0° C., 4-methoxybenzyl chloride (3.23 mL, 23.8 mmol) and the reaction was allowed to warm to rt. The reaction was then heated at 80° C. After 17 h, the reaction was allowed to cool to rt, quenched with saturated aqueous $NH_4Cl$ (100 mL) and extracted with EtOAc (3×100 mL). The combined extracts were washed with brine (100 mL), dried ($Na_2SO_4$), filtered and concentrated in vacuo. Purification of the residue by flash column chromatography on silica gel (2% EtOAc/Hex) afforded 7.02 g (94%) of the title compound.

Preparation 2

Isopropyl 5-chloromethylthiophene-2-carboxylate

Step 1. Preparation of the Bis-Isopropyl Ester

DBU (31.3 mL, 209 mmol) and 2-iodopropane (20.9 mL, 209 mmol) were added to a solution of thiophene-2,5-dicarboxylic acid (6.0 g, 34.9 mmol) in acetone (60 mL) at rt under nitrogen. After 21 h at rt, the reaction was quenched with saturated aqueous $NaHCO_3$ (300 mL) and extracted with EtOAc (3×150 mL). The combined extracts were washed with brine (200 mL), dried ($Na_2SO_4$), filtered and concentrated in vacuo to afford 7.59 g (85%) of the diester.

Step 2. Reduction to the Hydroxymethyl Ester

Sodium borohydride (3.36 g, 88.8 mmol) was added to a solution of the diester (7.59 g, 29.6 mmol) in $CH_2Cl_2$/MeOH (1:1, 100 mL) at 0° C. under nitrogen. The ice bath was removed and the reaction was allowed to stir at rt overnight. After 20.5 h at rt the reaction was concentrated in vacuo then aqueous 0.5 N HCl (100 mL) was added. The mixture was extracted with $CH_2Cl_2$ (3×100 mL). The combined extracts were dried ($Na_2SO_4$), filtered and concentrated in vacuo. Purification of the residue by flash column chromatography on silica (5%→60% EtOAc/Hex, gradient) afforded 738 mg (12%) of the alcohol.

Step 3. Conversion of the Alcohol to the Chloride

Methanesulfonyl chloride (0.67 mL, 8.1 mmol) and triethylamine (1.7 mL, 12.2 mmol) were added sequentially and dropwise to a solution of the alcohol (696 mg, 3.48 mmol) in CH₂Cl₂ (4.0 mL) at 0° C. under nitrogen. The ice bath was removed and the reaction was allowed to stir overnight at rt. After 17 h, the reaction was quenched with saturated aqueous NaHCO₃ (30 mL) and extracted with CH₂Cl₂ (3×50 mL). The combined extracts were dried (Na₂SO₄), filtered and concentrated in vacuo. Purification of the residue by flash column chromatography on silica (5% EtOAc/Hex) afforded 664 mg (87%) of the title compound.

Preparation 3

Methyl 5-allylthiophene-2-carboxylate

Step 1. Preparation of the Methyl Ester
Acetyl chloride (6.9 mL, 96.6 mmol) was added to a solution of 5-bromo-2-thiophenecarboxylic acid (4.0 g, 19.3 mmol) in methanol (30 mL) at rt. After 17 h at rt, the reaction was heated at reflux for 1.5 h to drive it to completion. The reaction was then cooled to rt and concentrated in vacuo to remove methanol. Saturated aqueous NH₄Cl (120 mL) was added and the mixture was extracted with CH₂Cl₂ (3×100 mL). The combined extracts were dried (Na₂SO₄), filtered and concentrated in vacuo to afford 3.57 g (84%) of the desired methyl ester as an off white solid.

Step 2. Allylation of the Bromothiophene
Isopropyl magnesium chloride (2.0 M in Et₂O, 8.9 mL, 17.8 mmol) was added to a solution of the bromide from step 1 (3.56 g, 16.1 mmol) in THF (10 mL) at −40° C. under nitrogen. The reaction mixture was stirred at −40° C. for 1 h, then copper (I) cyanide (144 mg, 1.61 mmol) and allyl bromide (3.0 mL, 35.4 mmol) were added sequentially. The reaction mixture was stirred at −40° C. for 1 h then was quenched with saturated aqueous NH₄Cl (100 mL) and extracted with EtOAc (3×100 mL). The combined extracts were washed with brine (100 mL), dried (Na₂SO₄), filtered and concentrated in vacuo. Purification of the residue by flash column chromatography on silica gel (5% EtOAc/Hex) afforded 2.45 g (83%) of the title compound as a pale yellow oil that solidified on standing.

Preparation 4

1-(1-(4-Methoxybenzyloxy-heptyl)-4-bromobenzene

Step 1. Hexyl Grignard Addition to 4-Bromobenzaldehyde
n-Hexyl magnesium bromide (2.0 M in Et₂O, 27 mL, 54 mmol) was added to a solution of 4-bromobenzaldehyde (5.0 g, 27 mmol) in THF (20 mL) at 0° C. under nitrogen. After 1.5 h at 0° C., the reaction was quenched slowly with 3 N HCl (20 mL) and concentrated in vacuo. The residue was diluted with water (30 mL) and extracted with Et₂O (3×150 mL). Combined extracts were dried (Na₂SO₄), filtered and concentrated in vacuo. Purification of the residue by flash column chromatography on silica gel (5%→10% EtOAc/Hex) afforded 5.6 g (76%) of 1-(4-bromophenyl)-heptan-1-ol.

Step 2. Protection of the Alcohol as its MPM Ether
Sodium hydride (60% wt. in oil, 0.991 g, 24.8 mmol) was added to a solution of the alcohol from step 1 (5.6 g, 20.6 mmol) in THF and DMF (2:1, 30 mL) at 0° C. under nitrogen. After 5 min at 0° C., the reaction was allowed to warm to rt and 4-methoxybenzyl chloride (3.4 mL, 25.0 mmol) was added. The reaction was then heated at 80° C. After 18 h at 80° C., the reaction was allowed to cool to rt, quenched with saturated aqueous NH₄Cl (50 mL) and concentrated in vacuo. The remainder was extracted with EtOAc (3×100 mL). The combined extracts were washed with water (2×100 mL) and brine (75 mL), then dried (Na₂SO₄), filtered and concentrated in vacuo. Purification of the residue by flash column chromatography on silica gel (2% EtOAc/Hex) afforded 7.5 g (93%) of the title compound.

Exemplary, non-limiting examples of compounds useful according to the present disclosure include the following compounds.

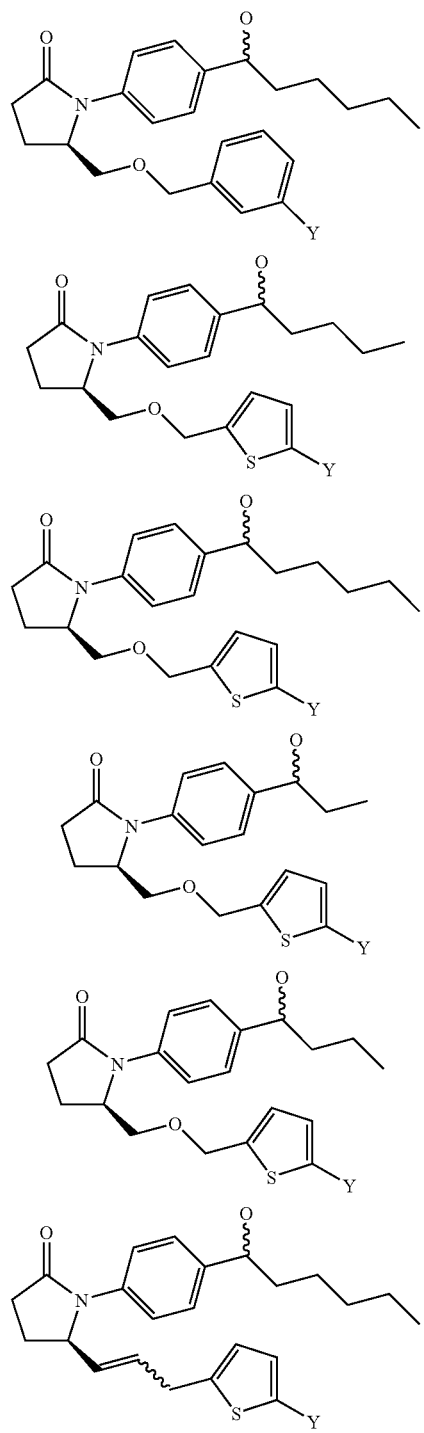

-continued

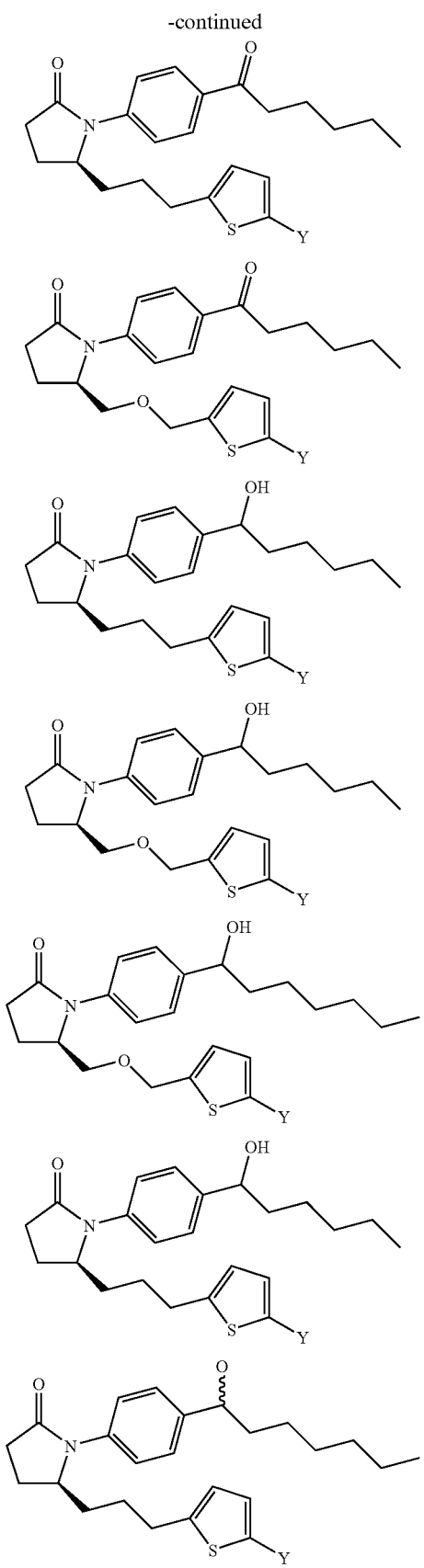

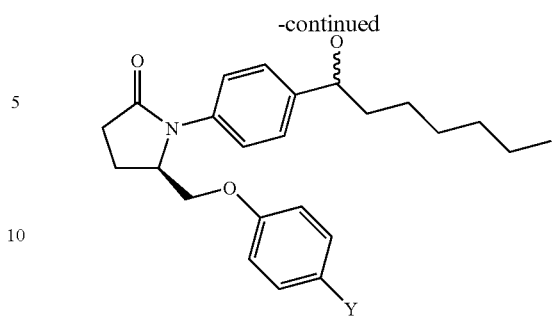

Composition Example

A composition comprising a compound listed above, wherein said composition is a liquid which is ophthalmically acceptable.

Medicament Examples

Use of a compound listed above in the manufacture of a medicament for the treatment of glaucoma or ocular hypertension in a mammal.

Use of a compound listed above in the manufacture of a medicament for the treatment of baldness in a mammal.

A medicament comprising a compound listed above, wherein said composition is a liquid which is ophthalmically acceptable.

Method Example

A method comprising administering a compound listed above to a mammal for the treatment of glaucoma or ocular hypertension.

A method comprising administering a compound listed above to a mammal for the treatment of baldness.

Kit Example

A kit comprising a composition comprising a compound listed above, a container, and instructions for administration of said composition to a mammal for the treatment of glaucoma or ocular hypertension.

A kit comprising a composition comprising a compound listed above, a container, and instructions for administration of said composition to a mammal for the treatment of baldness.

A "pharmaceutically acceptable salt" is any salt that retains the activity of the parent compound and does not impart any additional deleterious or untoward effects on the subject to which it is administered and in the context in which it is administered compared to the parent compound. A pharmaceutically acceptable salt also refers to any salt which may form in vivo as a result of administration of an acid, another salt, or a prodrug which is converted into an acid or salt.

Pharmaceutically acceptable salts of acidic functional groups may be derived from organic or inorganic bases. The salt may comprise a mono or polyvalent ion. Of particular interest are the inorganic ions lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

A "prodrug" is a compound which is converted to a therapeutically active compound after administration, and the term should be interpreted as broadly herein as is generally understood in the art. While not intending to limit the scope of the invention, conversion may occur by hydrolysis of an ester group or some other biologically labile group. Generally, but not necessarily, a prodrug is inactive or less active than the therapeutically active compound to which it is converted. Ester prodrugs of the compounds disclosed herein are specifically contemplated. An ester may be derived from a carboxylic acid of C1 (i.e. the terminal carboxylic acid of a natural prostaglandin), or an ester may be derived from a carboxylic acid functional group on another part of the molecule, such as on a phenyl ring. While not intending to be limiting, an ester may be an alkyl ester, an aryl ester, or a heteroaryl ester. The term alkyl has the meaning generally understood by those skilled in the art and refers to linear, branched, or cyclic alkyl moieties. $C_{1-6}$ alkyl esters are particularly useful, where alkyl part of the ester has from 1 to 6 carbon atoms and includes, but is not limited to, methyl, ethyl, propyl, isopropyl, n-butyl, sec-butyl, iso-butyl, t-butyl, pentyl isomers, hexyl isomers, cyclopropyl, cyclobutyl, cyclopentyl, cyclohexyl, and combinations thereof having from 1-6 carbon atoms, etc.

Those skilled in the art will readily understand that for administration or the manufacture of medicaments the compounds disclosed herein can be admixed with pharmaceutically acceptable excipients which per se are well known in the art. Specifically, a drug to be administered systemically, it may be confected as a powder, pill, tablet or the like, or as a solution, emulsion, suspension, aerosol, syrup or elixir suitable for oral or parenteral administration or inhalation.

For solid dosage forms or medicaments, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. The solid dosage forms may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release. Liquid pharmaceutically administrable dosage forms can, for example, comprise a solution or suspension of one or more of the presently useful compounds and optional pharmaceutical adjutants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 16th Edition, 1980. The composition of the formulation to be administered, in any event, contains a quantity of one or more of the presently useful compounds in an amount effective to provide the desired therapeutic effect.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

The amount of the presently useful compound or compounds administered is dependent on the therapeutic effect or effects desired, on the specific mammal being treated, on the severity and nature of the mammal's condition, on the manner of administration, on the potency and pharmacodynamics of the particular compound or compounds employed, and on the judgment of the prescribing physician. The therapeutically effective dosage of the presently useful compound or compounds may be in the range of about 0.5 or about 1 to about 100 mg/kg/day.

A liquid which is ophthalmically acceptable is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions of the present invention include, but are not limited to, benzalkonium chloride, chlorobutanol, thimerosal, phenylmercuric acetate and phenylmercuric nitrate. A useful surfactant is, for example, Tween 80. Likewise, various useful vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. A useful chelating agent is edetate disodium, although other chelating agents may also be used in place or in conjunction with it.

The ingredients are usually used in the following amounts:

| Ingredient | Amount (% w/v) |
| --- | --- |
| active ingredient | about 0.001-5 |
| preservative | 0-0.10 |
| vehicle | 0-40 |
| tonicity adjustor | 1-10 |
| buffer | 0.01-10 |
| pH adjustor | q.s. pH 4.5-7.5 |
| antioxidant | as needed |
| surfactant | as needed |
| purified water | as needed to make 100% |

Applications for Stimulating Hair Growth

In one embodiment, the compounds disclosed herein can be useful in the treatment of baldness and/or hair loss. Alopecia (baldness) is a deficiency of either normal or abnormal hair, and is primarily a cosmetic problem in humans. It is a deficiency of terminal hair, the broad diameter, colored hair that is readily seen. However, in the so called bald person, although there is a noticeable absence of terminal hair, the skin does contain vellus hair, which is a fine colorless hair which may require microscopic examination to determine its presence. This vellus hair is a precursor to terminal hair.

The compounds described herein can be used to stimulate, such as the conversion of vellus hair to growth as terminal hair, as well as increasing the rate of growth of terminal hair. The utility of the compounds described herein for the simulation of hair growth was discovered as follows.

In the course of treating patients having glaucoma, treatment may only be appropriate in one eye. Within the course of daily practice, it was discovered that a patient who had been treated with bimatoprost, a prostaglandin analogue, developed lashed that were longer, thicker, and fuller in the treated eye than in the non-treated eye. On examination, the difference was found to be very striking. The lashes were longer and had a fuller, denser appearance in the treated eye. The lash appearance on the lids of the treated eyes would have appeared quite attractive if it represented a bilateral phenomenon. As a result of its asymmetric nature, the long lashes on one side could be construed as disturbing from a cosmetic standpoint. A systemic examination was preformed as a result of the asymmetric phenomenon. It soon became apparent that this altered appearance was not an isolated finding. Comparison of the lids of patients who were taking bimatoprost in only one eye revealed subtle changes in the lashed and adjacent hairs of the bimatoprost-treated side in several patients. Definite differences could be identified to varying degrees in the lashes and adjacent hairs of all patients who were taking the drug on a unilateral basis for longer than 6 months.

The changes in the lashes were apparent on gross inspection in several patients once attention was focused on the issue. In those with light colored hair and lashes, the differences were only seen easily with the aid of the high magnification and lighting capabilities of the slit lamp biomicroscope. In the course of glaucoma follow-up examination, attention is generally immediately focused on the eye itself. As a result of the high power magnification needed only one eye is seen at a time and the eye is seen at a high enough power that the lashes are not in focus. At these higher powers, any lash asymmetry between the two eyes is not likely to be noticed except by careful systematic comparison of the lashes and adjacent hairs of the eyelids of the two eyes.

Observed parameters leading to the conclusion that more robust hair growth occurred in the treatment area following administration of the prostaglandin analogue were multiple. They included increased length of lashed, increased number of lashes along the normal lash line, increased thickness and luster of lashes, increased auxiliary lash-like terminal hair in transitional areas adjacent to areas of normal lash growth, increased auxiliary lash-like terminal hairs at the medial and lateral canthal area, increased pigmentation of the lashes, increased numbers, increased length, as well as increased luster, and thickness of fine hair on the skin of the adjacent lid, and finally, increased perpendicular angulation of lashes and lash-like terminal hairs. The conclusion that hair growth is stimulated by prostaglandin analogues such as bimatoprost is thus supported not by evidence of a difference in a single parameter, but is based on multiple parameters of hair appearance in treated versus control areas in many subjects.

The compounds described herein are prostaglandin analogues and therefore have similar activities as bimatoprost, contain structural similarities, and therefore are expected to stimulate hair growth and stimulation of the conversion of vellus hair to terminal hair. In one embodiment, the compounds described herein and their prodrugs can be used for the stimulation of hair growth. As used herein, hair growth includes hair associated with the scalp, eyebrows, eyelids, beard, and other areas of the skin of animals.

In one embodiment, the compound is mixed with a dermatologically compatible vehicle or carrier. The vehicle, which may be employed for preparing compositions as described herein, may comprise, for example, aqueous solutions such as e.g., physiological salines, oil solutions, or ointments. The vehicle furthermore may contain dermatologically compatible preservatives such as e.g., benzalkonium chloride, surfactants like e.g., polysorbate 80, liposomes or polymers, for example, methyl cellulose, polyvinyl alcohol, polyvinyl pyrrolidone and hyaluronic acid; these may be used for increasing the viscosity. Furthermore, it is also possible to use soluble or insoluble drug inserts when the drug is to be administered.

In one embodiment, dermatological compositions can be formulated for topical treatment for the stimulation of hair growth which comprises an effective hair growth simulating amount of one or more compounds as defined above and a dermatologically compatible carrier. Effective amounts of the active compounds may be determined by one of ordinary skill in the art, but will vary depending on the compound employed, frequency of application and desired result. The compound will generally range from about 0.0000001 to about 50% by weight of the dermatological composition. Preferably, the compound will range from about 0.001 to about 50% by weight of total dermatological composition, more preferably from about 0.1 to about 30% by weight of the composition.

In one embodiment, the application of the present compounds for stimulation of hair growth finds applications in mammalian species, including both humans and animals. In humans, the compounds described herein can be applied for example, to the scalp, face beard, head, pubic area, upper lip, eyebrows, and eyelids. In animal raised for their pelts, e.g., mink, the compounds described herein can be applied over the entire surface of the body to improve the overall pelt for commercial reasons. The process can also be used for cosmetic reasons in animals, e.g., applied to the skin of dogs and cats having bald patches due to mange or other diseases causing a degree of alopecia.

The pharmaceutical compositions contemplated for the stimulation of hair growth include pharmaceutical compositions suited for topical and local action. The term "topical" as employed herein relates to the use of a compound, as described herein, incorporated in a suitable pharmaceutical carrier, and applied at the site of thinning hair or baldness for exertion of local action. Accordingly, such topical compositions include those pharmaceutical forms in which the compound is applied externally by direct contact with the skin to be treated. Conventional pharmaceutical forms for this purpose include ointments, liniments, creams, shampoos, lotions, pastes, jellies, sprays, aerosols, and the like, and may be applied in patches or impregnated dressings depending on the part of the body to be treated. The term "ointment" embraces formulations (including creams) having oleaginous, water-soluble and emulsion-type bases, e.g., petrolatum, lanolin, polyethylene glycols, as well as mixtures of these.

Typically, the compounds can be applied repeatedly for the sustained period of time topically on the part of the body to be treated, for example, the eyelids, eyebrows, skin or scalp. The preferred dosage regimen will generally involve regular, such as daily, administration for a period of treatment of at least one month, more preferably at least three months, and most preferably, at least six months.

For topical use on the eyelids or eyebrows, the active compounds can be formulated in aqueous solutions, creams, ointments, or oils exhibiting physologicla acceptable osmolarity by addition of pharmaceutically acceptable buffers and salts such formulations may or may not, depending on the dispenser, contain preservatives such as benzalkonium chloride, chlorhexidine, chlorobutanol, parahydroxybenzoic acids and phenylmercuric salts such as nitrate, chloride, acetate, and borate, or antioxidants, as well as additives like EDTA, sorbitol, boric acid and the like as additives. Furthermore, particularly aqueous solutions may contain viscosity increasing agents such as polysaccharides, e.g., methylcellulose, mucopolysaccharides, e.g., hyaluronic acid and chondroitin sulfate, or poly alcohol, e.g., polyvinylalcohol. Various slow releasing gels and matricies may also be employed as well as soluble and insoluble ocular inserts, for instance, based on substances forming in situ gels. Depending on the actual formation and compound to be used, various amounts of the drug and different dose regimens may be employed. Typically, the daily amount of compound for treatment of the eyelid may be about 0.1 ng to about 100 mg per eyelid.

For topical use on the skin and scalp, the compound can be advantageously formulated using ointments, creams, liniments or patches as a carrier of the active ingredient. Also, these formulations may or may not contain preservatives, depending on the dispenser and nature of use. Such preservatives include those mentioned above, and methyl-, propyl-, or butyl-parahydroxybenzoic acid, betain, chlorhexidine, benzalkonium chloride, and the like. Various matricies for the slow release delivery may also be used. Typically, the dose to be applied on the scalp is in the range of about 0.1 ng to about 100 mg per day, more preferably about 1 ng to about 10 mg per day, and most preferably about 10 ng to about 1 mg per day depending on the compound and the formulation. To achieve the daily amount of medication depending on the formulation, the compound may be administered once or several times daily with or without antioxidants.

For topical use, creams, ointments, gels, solutions or suspensions, etc., containing the compound disclosed herein are employed. Topical formulations may generally be comprised of a pharmaceutical carrier, cosolvent, emulsifier, penetration enhancer, preservative system, and emollient.

The actual dose of the active compounds of the present invention depends on the specific compound, and on the condition to be treated; the selection of the appropriate dose is well within the knowledge of the skilled artisan.

The compounds disclosed herein are also useful in combination with other drugs useful for the treatment of glaucoma or other conditions.

For the treatment of glaucoma, combination treatment with the following classes of drugs are contemplated:

β-Blockers (or β-adrenergic antagonists) including carteolol, levobunolol, metiparanolol, timolol hemihydrate, timolol maleate, β1-selective antagonists such as betaxolol, and the like, or pharmaceutically acceptable salts or prodrugs thereof;

Adrenergic Agonists including non-selective adrenergic agonists such as epinephrine borate, epinephrine hydrochloride, and dipivefrin, and the like, or pharmaceutically acceptable salts or prodrugs thereof; and $\alpha_2$-selective adrenergic agonists such as apraclonidine, brimonidine, and the like, or pharmaceutically acceptable salts or prodrugs thereof;

Carbonic Anhydrase Inhibitors including acetazolamide, dichlorphenamide, methazolamide, brinzolamide, dorzolamide, and the like, or pharmaceutically acceptable salts or prodrugs thereof;

Cholinergic Agonists including direct acting cholinergic agonists such as carbachol, pilocarpine hydrochloride, pilocarbine nitrate, pilocarpine, and the like, or pharmaceutically acceptable salts or prodrugs thereof;

chlolinesterase inhibitors such as demecarium, echothiophate, physostigmine, and the like, or pharmaceutically acceptable salts or prodrugs thereof;

Glutamate Antagonists and other neuroprotective agents such as $Ca^{2+}$ channel blockers such as memantine, amantadine, rimantadine, nitroglycerin, dextrophan, detromethorphan, CGS-19755, dihydropyridines, verapamil, emopamil, benzothiazepines, bepridil, diphenylbutylpiperidines, diphenylpiperazines, HOE 166 and related drugs, fluspirilene, eliprodil, ifenprodil, CP-101,606, tibalosine, 2309BT, and 840S, flunarizine, nicardipine, nifedimpine, nimodipine, barnidipine, verapamil, lidoflazine, prenylamine lactate, amiloride, and the like, or pharmaceutically acceptable salts or prodrugs thereof;

Prostamides such as bimatoprost, or pharmaceutically acceptable salts or prodrugs thereof; and Prostaglandins including travoprost, UFO-21, chloprostenol, fluprostenol, 13,14-dihydro-chloprostenol, isopropyl unoprostone, latanoprost and the like.

Cannabinoids including CB1 agonists such as WIN-55212-2 and CP-55940 and the like, or pharmaceutically acceptable salts or prodrugs thereof.

For treatment of diseases affecting the eye including glaucoma, these compounds can be administered topically, periocularly, intraocularly, or by any other effective means known in the art.

In addition to the treatment of glaucoma, prostaglandin $EP_2$ selective agonists are believed to have several medical uses. For example, U.S. Pat. No. 6,437,146 teaches the use of prostaglandin $EP_2$ selective agonists "for treating or preventing inflammation and pain in joint and muscle (e.g., rheumatoid arthritis, rheumatoid spondylitis, osteoarthritis, gouty arthritis, juvenile arthritis, etc.), inflammatory skin condition (e.g., sunburn, burns, eczema, dermatitis, etc.), inflammatory eye condition (e.g., conjunctivitis, etc.), lung disorder in which inflammation is involved (e.g., asthma, bronchitis, pigeon fancier's disease, farmer's lung, etc.), condition of the gastrointestinal tract associated with inflammation (e.g., aphthous ulcer, Chrohn's disease, atrophic gastritis, gastritis varialoforme, ulcerative colitis, coeliac disease, regional ileitis, irritable bowel syndrome, etc.), gingivitis, inflammation, pain and tumescence after operation or injury, pyrexia, pain and other conditions associated with inflammation, allergic disease, systemic lupus crythematosus, scleroderma, polymyositis, tendinitis, bursitis, periarteritis nodose, rheumatic fever, Sjgren's syndrome, Behcet disease, thyroiditis, type I diabetes, diabetic complication (diabetic microangiopathy, diabetic retinopathy, diabetic neohropathy, etc.), nephrotic syndrome, aplastic anemia, myasthenia gravis, uveitis contact dermatitis, psoriasis, Kawasaki disease, sarcoidosis, Hodgkin's disease, Alzheimers disease, kidney dysfunction (nephritis, nephritic syndrome, etc.), liver dysfunction (hepatitis, cirrhosis, etc.), gastrointestinal dysfunction (diarrhea, inflammatory bowel disease, etc.) shock, bone disease characterized by abnormal bone metabolism such as osteoporosis (especially, postmenopausal osteoporosis), hypercalcemia, hyperparathyroidism, Paget's bone diseases, osteolysis, hypercalcemia of malignancy with or without bone metastases, rheumatoid arthritis, periodonritis, osteoarthritis, ostealgia, osteopenia, cancer cachexia, calculosis, lithiasis (especially, urolithiasis), solid carcinoma, mesangial proliferative glomerulonephritis, edema (e.g. cardiac edema, cerebral edema, etc.), hypertension such as malignant hypertension or the like, premenstrual tension, urinary calculus, oliguria such as the one caused by acute or chronic failure, hyperphosphaturia, or the like."

U.S. Pat. No. 6,710,072 teaches the use of EP2 agonists for the treatment or prevention of "osteoporosis, constipation, renal disorders, sexual dysfunction, baldness, diabetes, cancer and in disorder of immune regulation . . . various pathophysiological diseases including acute myocardial infarction, vascular thrombosis, hypertension, pulmonary hypertension, ischemic heart disease, congestive heart failure, and angina pectoris."

These compounds can also be used to treat or prevent conditions affecting the posterior part of the eye including maculopathies/retinal degeneration such as non-exudative age related macular degeneration (ARMD), exudative age related macular degeneration (ARMD), choroidal neovascularization, diabetic retinopathy, acute macular neuroretinopathy, central serous chorioretinopathy, cystoid macular edema, and diabetic macular edema; uveitis/retinitis/choroiditis such as acute multifocal placoid pigment epitheliopathy, Behcet's disease, birdshot retinochoroidopathy, infectious (syphilis, lyme, tuberculosis, toxoplasmosis), intermediate uveitis (pars planitis), multifocal choroiditis, multiple evanescent white dot syndrome (mewds), ocular sarcoidosis, posterior scleritis, serpiginous choroiditis, subretinal fibrosis and uveitis syndrome, Vogt-Koyanagi- and Harada syndrome; vasuclar diseases/exudative diseases such as retinal arterial occlusive disease, central retinal vein occlusion, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angiitis, sickle cell retinopathy and other hemoglobinopathies, angioid streaks, familial exudative vitreoretinopathy, and Eales disease; traumatic/surgical conditions such as sympathetic ophthalmia, uveitic retinal disease, retinal detachment, trauma, conditions caused by laser, conditions caused by photodynamic therapy, photocoagulation, hypoperfusion during surgery, radiation retinopathy, and bone marrow transplant retinopathy; proliferative disorders such as proliferative vitreal retinopathy and epiretinal membranes, and proliferative diabetic retinopathy; infectious disorders such as ocular histoplasmosis, ocular toxocariasis, presumed ocular histoplasmosis syndrome (POHS), endophthalmitis, toxoplasmosis, retinal diseases associated with HIV infection, choroidal disease associate with HIV infection, uveitic disease associate with HIV infection, viral retinitis, acute retinal necrosis, progressive outer retinal necrosis, fungal retinal diseases, ocular syphilis, ocular tuberculosis, diffuse unilateral subacute neuroretinitis, and myiasis; genetic disorders such as retinitis pigmentosa, systemic disorders with accosiated retinal dystrophies, congenital stationary night blindness, cone dystrophies, Stargardt's disease and fundus flavimaculatus, Best's disease, pattern dystrophy of the retinal pigmented epithelium, X-linked retinoschisis, Sorsby's fundus dystrophy, benign concentric maculopathy, Bietti's crystalline dystrophy, and pseudoxanthoma elasticum; retinal tears/holes such as retinal detachment, macular hole, and giant retinal tear; tumors such as retinal disease associated with tumors, congenital hypertrophy of the retinal pigmented epithelium, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, and intraocular lymphoid tumors; and miscellaneous other diseases affecting the posterior part of the eye such as punctate inner choroidopathy, acute posterior multifocal placoid pigment epitheliopathy, myopic retinal degeneration, and acute retinal pigement epitheliitis. Preferably, the disease or condition is retinitis pigmentosa, proliferative vitreal retinopathy (PVR), age-related macular degeneration (ARMD), diabetic retinopathy, diabetic macular edema, retinal detachment, retinal tear, uveitus, or cytomegalovirus retinitis.

These compounds are also useful in treating asthma.

A person of ordinary skill in the art understands the meaning of the stereochemistry associated with the hatched wedge/solid wedge structural features. For example, an introductory organic chemistry textbook (Francis A. Carey, Organic Chemistry, New York: McGraw-Hill Book Company 1987, p. 63) states "a wedge indicates a bond coming from the plane of the paper toward the viewer" and the hatched wedge, indicated as a "dashed line", "represents a bond receding from the viewer." Unless stereochemistry is explicitly depicted, a structure is intended to include every possible stereoisomer, both pure or in any possible mixture. Unless stereochemistry is explicitly depicted, a structure is intended to include every possible stereoisomer, both pure or in any possible mixture.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the appended claims.

What is claimed is:
1. A compound according to a formula selected from
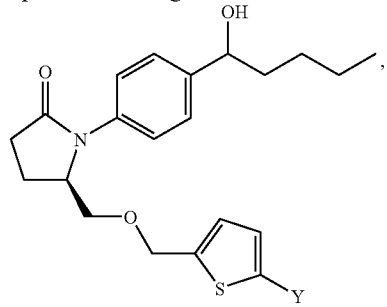,
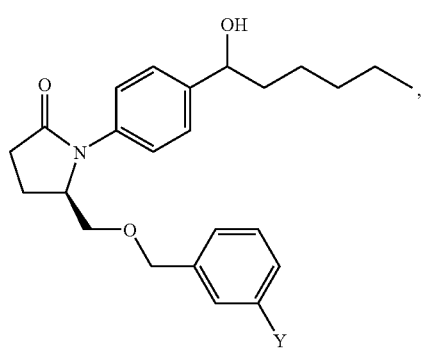,
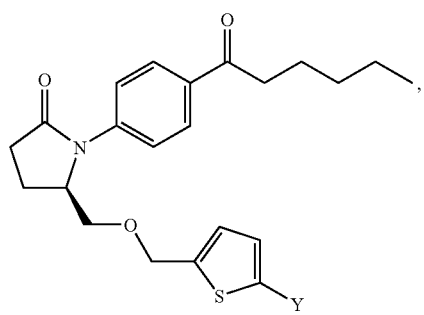,
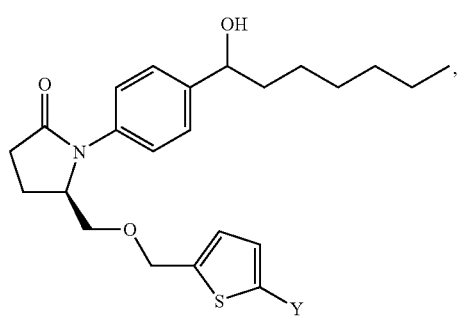,
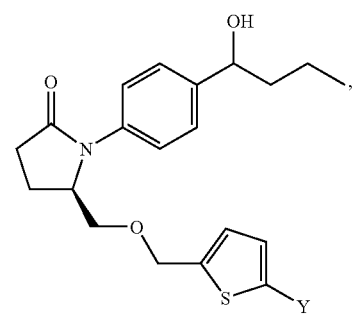,
-continued
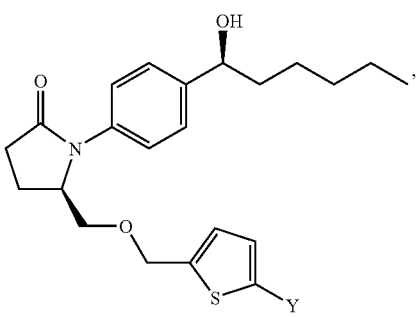,
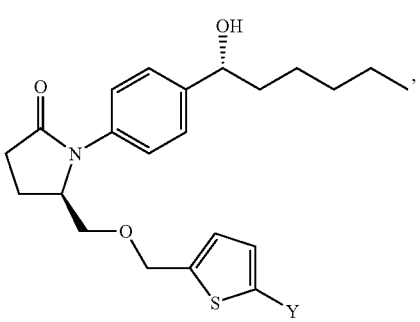,
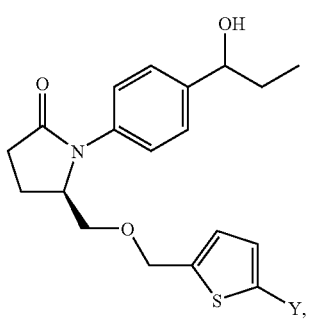,
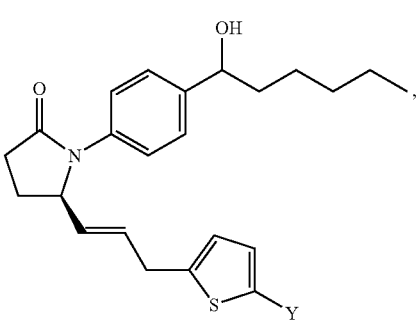,
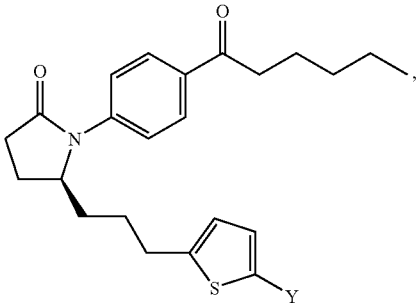,

-continued
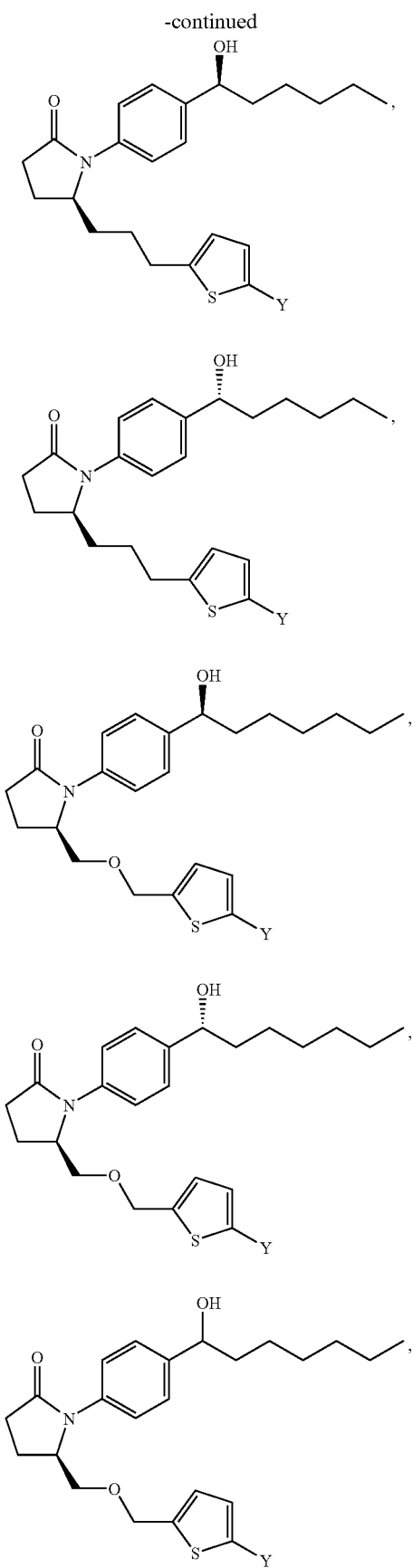
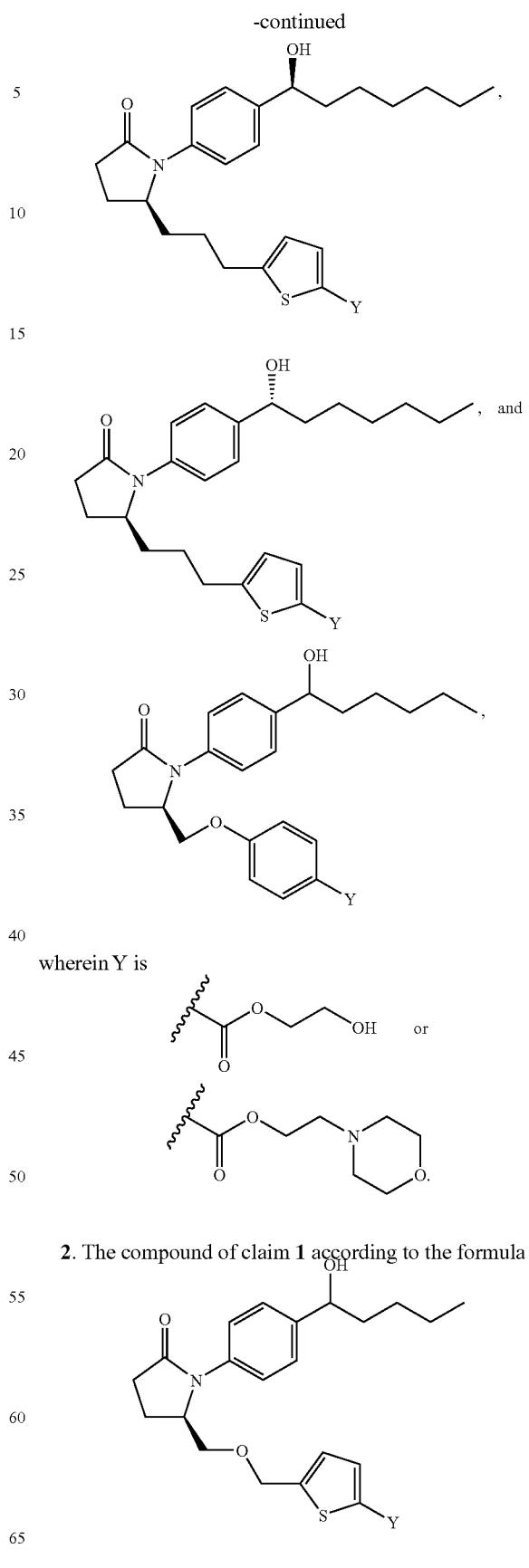
wherein Y is
2. The compound of claim 1 according to the formula
or a pharmaceutically acceptable salt or a prodrug thereof.

3. The compound of claim 1 according to the formula

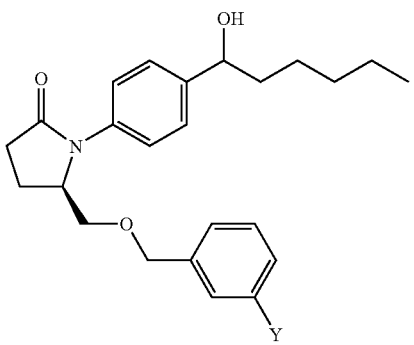

or a pharmaceutically acceptable salt or a prodrug thereof.

4. The compound of claim 1 according to the formula

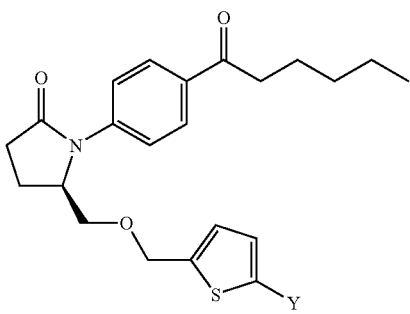

or a pharmaceutically acceptable salt or a prodrug thereof.

5. The compound of claim 1 according to the formula

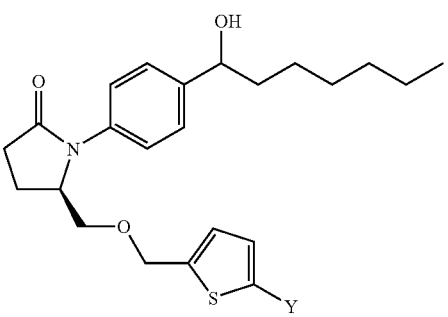

or a pharmaceutically acceptable salt or a prodrug thereof.

6. The compound of claim 1 according to the formula

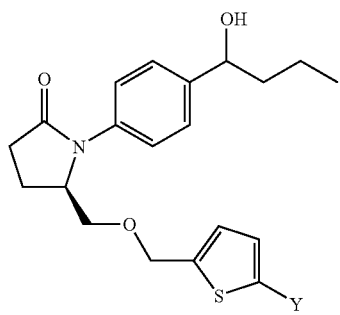

or a pharmaceutically acceptable salt or a prodrug thereof.

7. The compound of claim 1 according to the formula

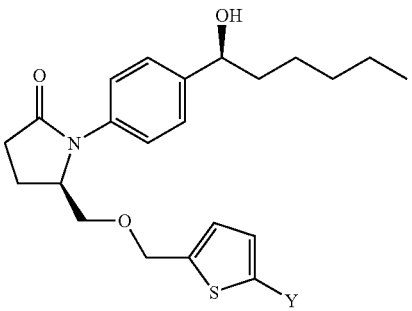

or a pharmaceutically acceptable salt or a prodrug thereof.

8. The compound of claim 1 according to the formula

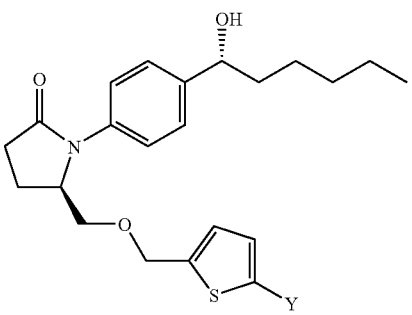

or a pharmaceutically acceptable salt or a prodrug thereof.

9. The compound of claim 1 according to the formula

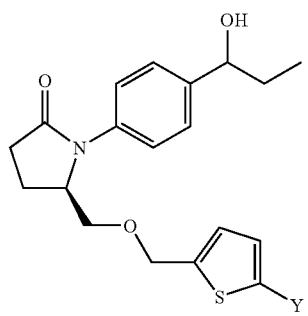

or a pharmaceutically acceptable salt or a prodrug thereof.

10. The compound of claim 1 according to the formula

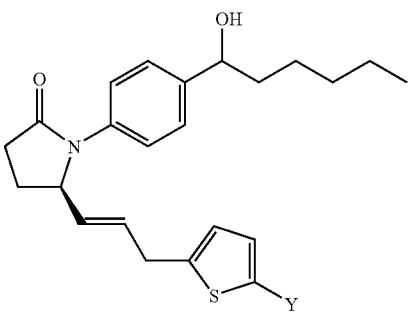

or a pharmaceutically acceptable salt or a prodrug thereof.

11. The compound of claim 1 according to the formula

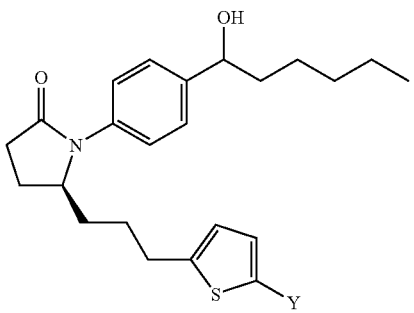

or a pharmaceutically acceptable salt or a prodrug thereof.

12. The compound of claim 1 according to the formula

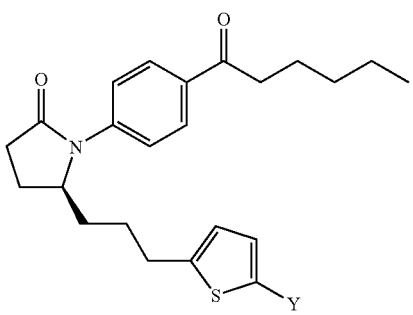

or a pharmaceutically acceptable salt or a prodrug thereof.

13. The compound of claim 1 according to the formula

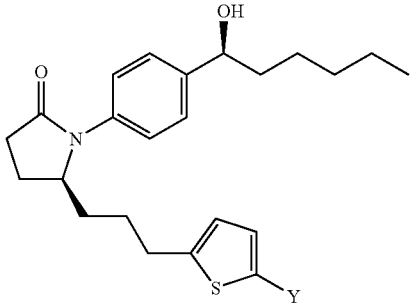

or a pharmaceutically acceptable salt or a prodrug thereof.

14. The compound of claim 1 according to the formula

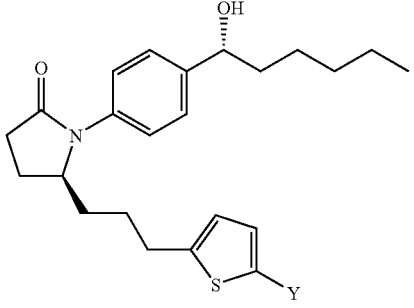

or a pharmaceutically acceptable salt or a prodrug thereof.

15. The compound of claim 1 according to the formula

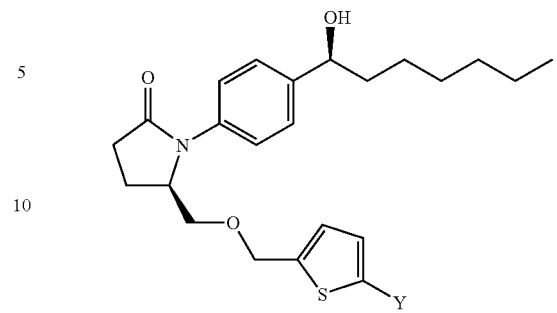

or a pharmaceutically acceptable salt or a prodrug thereof.

16. The compound of claim 1 according to the formula

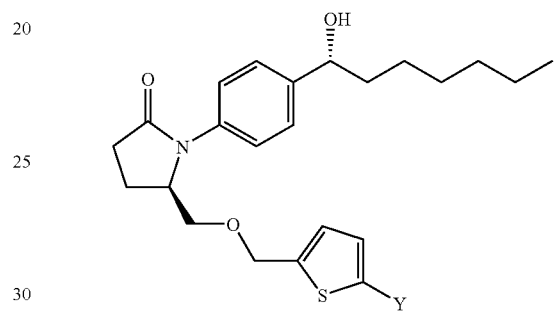

or a pharmaceutically acceptable salt or a prodrug thereof.

17. The compound of claim 1 according to the formula

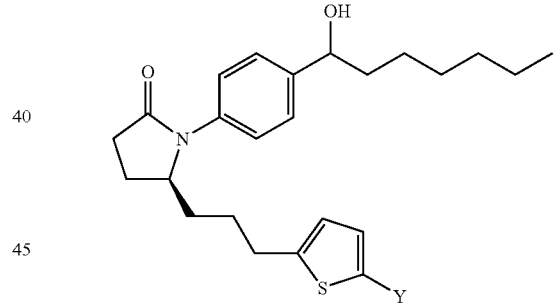

or a pharmaceutically acceptable salt or a prodrug thereof.

18. The compound of claim 1 according to the formula

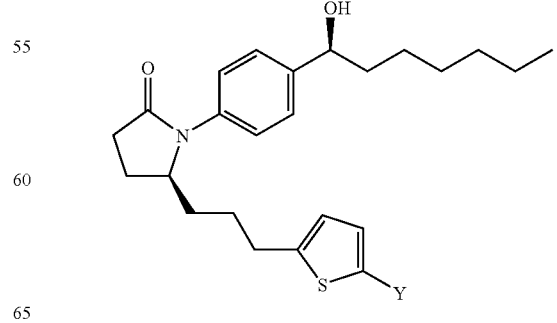

or a pharmaceutically acceptable salt or a prodrug thereof.

19. The compound of claim 1 according to the formula
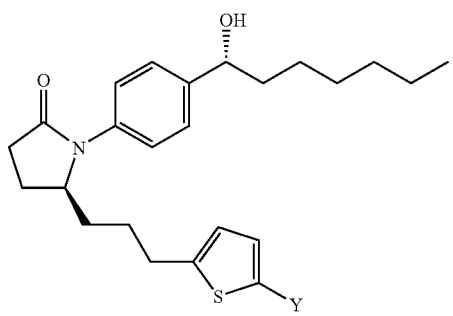
or a pharmaceutically acceptable salt or a prodrug thereof.
20. The compound of claim 1 according to the formula
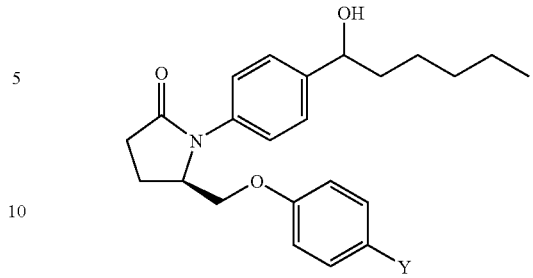
or a pharmaceutically acceptable salt or a prodrug thereof.
21. A method of treating baldness using a compound selected from any one of claims 1 to 20.
* * * * *